United States Patent
Barker et al.

(10) Patent No.: US 6,479,527 B1
(45) Date of Patent: Nov. 12, 2002

(54) BICYCLIC PYRROLE DERIVATIVES AS MCP-1 INHIBITORS

(75) Inventors: Andrew J. Barker; Alan W Faull; Jason G. Kettle, all of Macclesfield (GB)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 09/626,378

(22) Filed: Jul. 26, 2000

(30) Foreign Application Priority Data

Feb. 17, 1998 (GB) ................................. 980322

(51) Int. Cl.$^7$ ................. A61K 31/407; A61K 31/4188; A61K 31/429; C07D 487/04; C07D 513/04
(52) U.S. Cl. ........................ 514/367; 514/382; 514/393; 514/412; 514/414; 548/153; 548/252; 548/303.1; 548/453
(58) Field of Search ............................... 548/453, 303.1, 548/153, 252; 514/412, 414, 393, 367, 382

(56) References Cited

U.S. PATENT DOCUMENTS

| | | | |
|---|---|---|---|
| 4,608,384 A | 8/1986 | Wierzbicki et al. | 514/413 |
| 4,751,231 A | 6/1988 | Halczenko et al. | 514/412 |

FOREIGN PATENT DOCUMENTS

| | | |
|---|---|---|
| EP | 0 114 014 | 7/1984 |
| FR | 2 565 981 | 12/1985 |
| WO | WO 96/18393 | 6/1996 |
| WO | WO 96/31492 | 10/1996 |
| WO | WO 97/12613 | 4/1997 |
| WO | WO 98/06703 | 2/1998 |

OTHER PUBLICATIONS

Bobošik et al., "Synthesis of N–Phenylsulfonyl Protected Furo[3,2–b]pyrroles", Collect. Czech. Chem. Commun., vol. 59, 1994, pp. 499–502.
Hartman et al., "The Synthesis of 5–alkylaminomethylthieno[2,3–b]pyrrole–5–sulfonamides", Heterocycles, vol. 29, 1989, pp. 1943–1949.
Krutošiková et al., "Derivatives of Fuor[3,2–b]pyrrole", Collect. Czech. Chem. Commun., vol. 59, 1994, pp. 473–481.
Krutošiková "Subsituted Benzylfuro[3,2–b]pyrroles", Collect. Czech. Chem. Commun., vol. 57, 1992, pp. 1487–1494.
Krutošiková et al., "Substituted Vinyl Azides in Synthesis of Furo[3,2–b:4,5–b]–dipyrroles and Pyrrolo[2',3':4,5]Furo[3, 2–c]pyridines", Heterocycles. vol. 37, No. 3, 1994, pp. 1695–1700.
Krutošiková et al., "Synthesis and Reactions of Furo[3,2–b] pyurrole Type Aldehydes", Czech. Chem. Commun., vol.58, 1993, pp. 2139–2149.
Krutosikova et al., "Condensed O–, N–Heterocycles by the Transformation of Azidoacrylates", Monatshefte für Chemie 123, 1992, pp. 807–815.
Krutošiková et al., "Substituted Vinyl Azides in the Synthesis of Condensed Nitrogen Heterocycles", Chem. Papers, vol. 48, 1994, pp. 268–273.
Krutošiková et al., "Reactions of Methyl 2–Formylfuro[3, 2–b]pyrrole–5–carboxylates", Chem. Papers. vol. 50, 1996, pp. 72–76.
Dandárová et al., "Reference Data", Magnetic Resonance in Chemistry, vol. 28, 1990, pp. 830–831.
Derwent Abstract for JP 63284177 including Chemical Abstract Registry Records for specific compounds indexed, 1989.
Derwent World Patent Index recrod, JAPIO record and Chemical Abstract for Molecules (1997), 2(4), 69–79, including Chemical Abstract Registry records for specific compounds indexed.

*Primary Examiner*—Laura L. Stockton
(74) *Attorney, Agent, or Firm*—Pillsbury Winthrop LLP

(57) ABSTRACT

A pharmaceutical composition comprising a compound of formula (I):

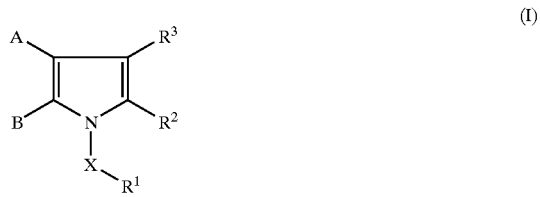

(I)

or a pharmaceutically acceptable salt, ester or amide thereof, which is an inhibitor of monocyte chemoattractant protein-1 and wherein A and B together form an optionally substituted 5-member aromatic ring which includes at least one heteroatom; $R^1$ is an optionally substituted aryl or heteroaryl ring; $R^2$ is selected from a range of organic groups including carboxy, and $R^3$ is hydrogen, or a range of organic groups; in combination with a pharmaceutically acceptable carrier. Certain compounds of formula (I) are novel and these form a further aspect of the invention.

17 Claims, No Drawings

BICYCLIC PYRROLE DERIVATIVES AS MCP-1 INHIBITORS

This application is the national phase of international application PCT/GB99/00335 filed Feb. 2, 1999 which designated the U.S.

The present invention relates to pharmaceutical compositions which comprise anti-inflammatory and immunomodulatory compounds that act via antagonism of the CCR2 receptor, (also known as the MCP-1 receptor), leading inter alia to inhibition of Monocyte Chemoattractant Protein-1 (MCP-1). These compounds contain a bicyclic aromatic moiety. The invention further relates to novel compounds for use in the compositions, to processes for their preparation. to intermediates useful in their preparation and to their use as therapeutic agents.

MCP-1 is a member of the chemokine family of pro-inflammatory proteins which mediate leukocyte chemotaxis and activation. MCP-1 is a C—C chemokine which is one of the most potent and selective T-cell and monocyte chemoattractant and activating agents known. MCP-1 has been implicated in the pathophysiology of a large number of inflammatory diseases including rheumatoid arthritis, glomerular nephritides, lung fibrosis, restenosis (International Patent Application WO 94/09128), alveolitis (Jones et al., 1992, J. Immunol., 149, 2147) and asthma. Other disease areas where MCP-1 is thought to play a part in their pathology are atherosclerosis (e.g. Koch et al., 1992, J. Clin. Invest., 90, 772–779), psoriasis (Deleuran et al., 1996, J. Dermatological Science, 13, 228–236), delayed-type hypersensitivity reactions of the skin, inflammatory bowel disease (Grimm et al., 1996, J. Leukocyte Biol., 59, 804–812), multiple sclerosis and brain trauma (Berman et al, 1996, J. Immunol., 156, 3017–3023). An MCP-1 inhibitor may also be useful to treat stroke, reperfusion injury, ischemia, myocardial infarction and transplant rejection.

MCP-1 acts through the CCR2 receptor. MCP-2 and MCP-3 may also act, at least in part, through this receptor. Therefore in this specification, when reference is made to "inhibition or antagonism of MCP-1" or "MCP-1 mediated effects" this includes inhibition or antagonism of MCP2 and/or MCP-3 mediated effects when MCP-2 and/or MCP-3 are acting through the CCR2 receptor.

WO-9631492 describes a range of compounds including bicyclic compounds which are inhibitors of endothelin receptors. JP-3284177 discloses the preparation of certain formyl substituted pyrrolo-pyrroles for use in a range of applications. In addition, U.S. Pat. No.4,751,231 describes the preparation of substituted thienosulphonamides as anti-glaucoma agents.

The applicants have found a class of compounds containing a bicyclic moiety which have useful inhibitory activity against MCP-1.

The present invention provides a pharmaceutical composition comprising a compound of formula (I):

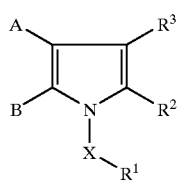

(I)

or a pharmaceutically acceptable salt or esters of amides thereof, which is an inhibitor of monocyte chemoattractant protein- I and wherein A and B together with the carbon atoms to which they are attached, form an optionally substituted 5 membered aromatic ring which includes at least one heteroatom;

X is $CH_2$ or $SO_2$;

$R^1$ is an optionally substituted aryl or heteroaryl ring;

$R^2$ is carboxy, cyano, —C(O)CH$_2$OH, —CONHR$^4$, —SO$_2$NHR$^5$, tetrazol-5-yl, SO$_3$H, or a group of formula (VI):

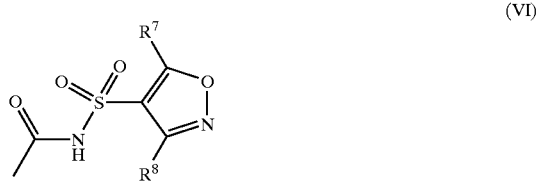

(VI)

where $R^4$ is selected from hydrogen, alkyl, aryl, cyano, hydroxy, —SO$_2$R$^9$ where R$^9$ is alkyl, aryl, heteroaryl, or haloalkyl, or R$^4$ is a group-(CHR$^{10}$)$_r$—COOH where r is an integer of 1–3 and each $R^{10}$ group is independently selected from hydrogen or alkyl; $R^5$ is alkyl, optionally substituted aryl such as optionally substituted phenyl or optionally substituted heteroaryl such as 5 or 6 membered heteroaryl groups, or a group COR$^6$ where $R^6$ is hydrogen, alkyl, aryl, heteroaryl or haloalkyl; $R^7$ and $R^8$ are independently selected from hydrogen or alkyl, particularly $C_{1-4}$ alkyl; and $R^3$ is hydrogen, a functional group, optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy, optionally substituted cycloalkyl; in combination with a pharmaceutically acceptable carrier or diluent.

Suitably the composition comprises a compound of formula (I) or a salt or in vivo hydrolysable ester thereof.

Compounds of formula (I) are inhibitors of monocyte chemoattractant protein-1. In addition, they appear to inhibit RANTES induced chemotaxis. RANTES (Regulated upon Activation, Normal T-cell Expressed and Secreted) is another chemokine from the same family as MCP-1, with a similar biological profile, but acting though the CCR1 receptor. As a result, these compounds can be used to treat disease mediated by these agents, in particular inflammatory disease.

Example of such compounds are compounds where A, B, X, $R^1$ and $R^3$ are as defined above, and where $R^2$ is as defined above but $R^4$ is selected from cyano, hydroxy, —SO$_2$R$^9$ where R$^9$ is alkyl, aryl, hcteroaryl, or haloalkyl, or $R^4$ is a group-(CHR$^{10}$)$_r$—COOH where r is an integer of 1–3 and each $R^{10}$ group is independently selected from hydrogen or alkyl; $R^5$ is optionally substituted phenyl or optionally heteroaryl groups, or a group COR$^6$ where $R^6$ is alkyl, aryl, heteroaryl or haloalkyl; $R^7$ and $R^8$ are independently selected from hydrogen or alkyl, particularly $C_{1-4}$ alkyl.

In this specification the term "heteroatom" refers to non-carbon atoms such as oxygen, nitrogen or sulphur atoms. The term 'alkyl' when used either alone or as a suffix includes straight chain and branched structures. These groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" and "alkanoyl" comprise alkyl moieties as defined above, attached to the appropriate functionality.

The term "halo" includes fluoro, chloro, bromo and iodo. References to aryl groups include aromatic carbocylic groups such as phenyl and naphthyl. The term "heterocyclyl" includes aromatic or non-aromatic rings, for example containing from 4 to 20, suitably from 5 to 10 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, iosquinolinyl, quinoxalinyl, benzthiazolyl, benzoxazolyl, benzothienyl or benzofuryl.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. For example, these may be alkyl, alkenyl, alkynyl, aryl, heterocyclyl, alkoxy, aralkyl, cycloalkyl, cycloalkenyl or cycloalkynyl.

The term "functional group" refers to reactive substituents. They may comprise electron-donating or electron-withdrawing. Examples of such groups include halo, cyano, nitro, $C(O)_nR^{11}$, $OR^{11}$, $S(O)_mR^{11}$, $NR^{12}R^{12'}$, $C(O)NR^{12}R^{12'}$, $OC(O)NR^{12}R^{12'}$, —CH=NOR$^{11}$, —NR$^{12}$C(O)$_nR^{11}$, —NR$^{11}$CONR$^{12}R^{12'}$, —N=CR$^{12}R^{12'}$, $S(O)_mNR^{12}R^{12'}$ or —NR$^{12}$S(O)$_mR^{11}$ where $R^{11}$, $R^{12}$ and $R^{12'}$ are independently selected from hydrogen or optionally substituted hydrocarbyl, or $R^{12}$ and $R^{12'}$ together form an optionally substituted ring which optionally contains further heteroatoms such as $S(O)_m$, oxygen and nitrogen, n is an integer of 1 or 2, m is 0 or an integer of 1–3. Where functional groups comprise $S(O)_mNR^{12}R^{12'}$ or —NR$^{12}$S(O)$_mR^{11}$, m is generally an integer from 1–3. For the avoidance of doubt, where $R^{12}$ and $R^{12'}$ together form an optionally substituted ring, the ring will comprise a non-aromatic heterocyclyl group as defined above.

Suitable optional substituents for hydrocarbyl groups $R^{11}$, $R^{12}$ and $R^{12'}$ include halo, perhaloalkyl such as trifluoromethyl, mercapto, hydroxy, alkoxy, oxo, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, alkylamido, oximino (for example hydroxyimino or alkyloxyimino) or $S(O)_mR^y$ where m is as defined above and $R^y$ is alkyl.

Examples of optional substituents for the group A-B include functional groups as defined above or optionally substituted hydrocarbyl groups or optionally substituted heterocyclic groups. A particular substituent for the A-B group is a group of sub-formula (IV).

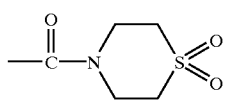

(IV)

Suitably A and B together with the carbon atoms to which they are attached form a 5 membered heteroaryl ring of any one of the sub-formulae:

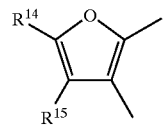 (i)

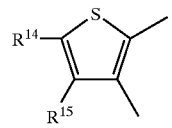 (ii)

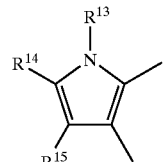 (iii)

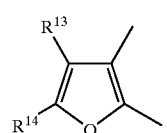 (iv)

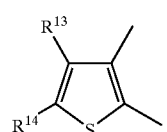 (v)

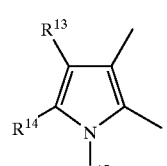 (vi)

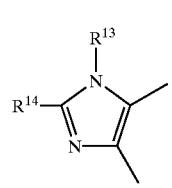 (vii)

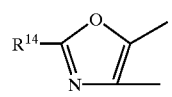 (viii)

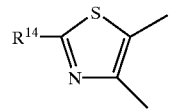 (ix)

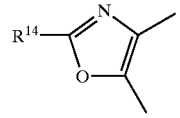 (x)

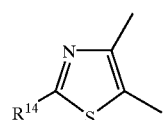 (xi)

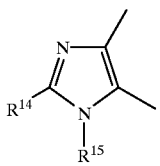
(xii)

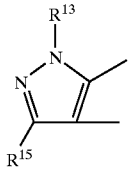
(xiii)

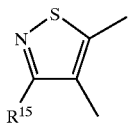
(xiv)

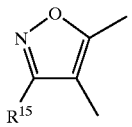
(xv)

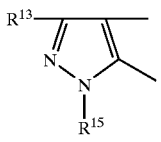
(xvi)

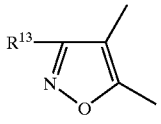
(xvii)

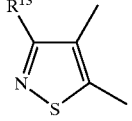
(xviii)

where $R^{13}$, $R^{14}$ and $R^{15}$ are as independently selected from hydrogen or a substituent group.

Suitably substituents $R^{13}$, $R^{14}$, $R^{15}$ include functional groups as defined above or optionally substituted hydrocarbyl groups.

Suitable hydrocarbyl groups for $R^{13}$, $R^{14}$, $R^{15}$ include alkyl, cycloalkyl, alkenyl, cycloalkenyl, alkynyl, cycloalkynyl.

Particular substituent groups for the A-B ring include trifluoromethyl; optionally substituted $C_{1-4}$alkyl such as aralkyl, carboxyalkyl or the amide derivative thereof; halo; hydroxy; $C_{1-4}$alkoxy; $C_{1-4}$alkanoyl; $C_{1-4}$alkanoyloxy; amino; cyano; $C_{1-4}$alkylamino; di($C_{1-4}$alkyl)amino; $C_{1-4}$alkanoylamino; nitro; carbamoyl; $C_{1-4}$alkoxycarbonyl; thiol; $C_{1-4}$alkylsulphanyl; $C_{1-4}$alkylsulphinyl; $C_{1-4}$alkylsulphonyl; sulphonamido or alkyl or aryl sulphonamido, carbamoyl$C_{1-4}$alkyl; N—($C_{1-4}$alkyl) carbamoyl$C_{1-4}$alkyl; N—($C_{1-4}$alkyl)$_2$carbamoyl-$C_{1-4}$alkyl; hydroxy$C_{1-4}$alkyl; $C_{1-4}$alkoxy$C_{1-4}$alkyl; mono-or di-alkyl or aryl substituted urea; morpholino; thiomorpholino; oxythiomorpholino; pyrrolidinyl; carboxy$C_{1-4}$alkylamino; $R^{16}$, —NHR$^{17}$ and —OR$^{17}$ (where $R^{16}$ and $R^{17}$ are independently selected from optionally substituted phenyl and an optionally substituted 5- or 6-membered heteroaryl ring).

Suitable optional substituents for $R^{16}$ and $R^{17}$ include those listed above for $R^{11}$, $R^{12}$ or $R^{12'}$. Suitable optional substituents for $R^{16}$ and $R^{17}$ also include those listed herein for $R^1$. Alkyl or aryl sulphonamido substituents may themselves be optionally substituted, for example by substituents listed above for $R^{11}$, $R^{12}$ or $R^{12'}$ or listed herein for $R^1$.

Examples of compounds of formula (I) are those where the ring A-B carries at least one substituent.

Suitably, when A-B forms a group of sub-formula (iii) above, and $R^{15}$ is hydrogen, $R^{14}$ is other than formyl, and/or $R^{13}$ is other than hydrogen, alkyl or aralkyl.

Suitably, where A-B forms a group of sub-formula (v) above, $R^{13}$ is other than an amidino group.

Substituents are suitably arranged at or close to the side of the ring designated "A" in preference to the "B" position. Thus, in compounds of subformulae (i) to (xviii) above, $R^{13}$ and/or $R^{14}$ where present are suitably other than hydrogen, most preferably $R^{13}$ is other than hydrogen. The positions closest to the "B" position are preferably hydrogen. Therefore, in the above sub-formulae (i) to (xviii), $R^{15}$ is most preferably hydrogen.

Preferred substituents for the A-B ring and therefore, preferred examples of $R^{13}$, $R^{14}$ and $R^{15}$ include $C_{1-4}$ alkyl, in particular methyl, which alkyl group is optionally substituted with hydroxy, amino or mono or di-$C_{1-4}$ alkylamino such as methylamino or dimethylamino; cyano; halogen in particular bromine; thienyl; tetrazolyl; phenyl optionally substituted with amino; $C_{1-4}$ alkoxy, in particular methoxy; carboxy or carboxamido.

Preferred substituents for the A-B ring where present and therefore, preferred examples of $R^{13}$, $R^{14}$ and $R^{15}$ are $C_{1-4}$alkyl, in particular methyl.

Suitable optional substituents for $R^1$ in formula (I) include those listed above for $R^{11}$, $R^{12}$ and $R^{12'}$ as well as alkyl, alkenyl, or alkynyl.

Suitable optional substituents for alkyl, alkenyl, alkynyl, groups $R^3$ include those listed above for $R^{11}$, $R^{12}$ and $R^{12'}$, and for aryl, aralkyl, cycloalkyl or heterocyclyl groups $R^3$, the substituents may be as listed herein for $R^1$.

Suitably X is $CH_2$.

Suitably $R^1$ is an optionally substituted phenyl, naphthyl, furyl, pyridyl or thienyl ring, and preferably a substituted phenyl or pyridyl ring.

Preferably $R^1$ is substituted by at least one substituent, particularly when $R^1$ is phenyl.

Particular substituents for $R^1$ include trifluoromethyl, $C_{1-4}$alkyl, halo, trifluoromethoxy, $C_{1-4}$alkoxy, $C_{1-4}$alkanoyl, $C_{1-4}$alkanoyloxy, $C_{1-4}$alkylamino, di($C_{1-4}$alkyl)amino, $C_{1-4}$alkanoylamino, nitro, carboxy, carbamoyl, $C_{1-4}$alkoxycarbonyl, thiol, $C_{1-4}$alkylsulphanyl, $C_{1-4}$alkylsulphinyl, $C_{1-4}$alkylsulphonyl, sulphonamido, carbamoyl$C_{1-4}$alkyl, N—($C_{1-4}$alkyl)carbamoyl$C_{1-4}$alkyl, N—($C_{1-4}$alkyl)$_2$carbamoyl-$C_{1-4}$alkyl, hydroxy$C_{1-4}$alkyl or $C_{1-4}$alkoxy$C_{1-4}$alkyl.

Additionally or alternatively, two such substituents together may form a divalent radical of the formula —O(CH$_2$)$_{1-4}$O— attached to adjacent carbon atoms on the $R^1$ ring.

Preferred substituents for $R^1$ are one or more non-polar substituents such as halo.

In particular, $R^1$ is substituted by one or more halo groups, in particular chlorine. A particular example of an $R^1$ group is 3,4-dichlorophenyl, 3,4difluorophenyl, 3-fluoro-4-chlorophenyl, 3-chloro-4-fluorophenyl or 2,3-dichloropyrid-5-yl.

Preferably, $R^1$ is 3,4-dichlorophenyl.

Examples of groups $R^2$ include carboxy, tetrazol-5-yl, cyano, $SO_3H$, —$SO_2NHR^5$ —$CONHR^4$, or a group of formula (VI).

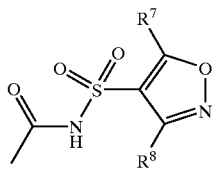

(VI)

where $R^5$ is as defined above, $R^7$ and $R^8$ are independently selected from hydrogen or alkyl, particularly $C_{1-4}$ alkyl, $R^4$ is cyano, OH, —$SO_2$—$C_{1-4}$alkyl (where the alkyl group is optionally substituted with halo such as fluoro, particularly at the alpha position), —$SO_2CF_3$, —$SO_2$-pheny[, —$(CHR^{10})_r$—COOH, where r is 1–3 and each $R^{10}$ group is independently selected from hydrogen or alkyl such as $C_{1-4}$ alkyl.

Preferably $R^2$ is carboxy or a pharmaceutically acceptable salt or ester thereof, such as a $C_{1-4}$ alkyl ester, and particularly carboxy or a pharmaceutically acceptable salt thereof, especially carboxy.

Suitable groups $R^3$ include hydrogen, fluoro, chloro, bromo, iodo, methyl, cyano, trifluoromethyl, hydroxymethyl, alkoxyalkyl such as $C_{1-4}$alkoxymethyl, methoxy, benzyloxy, carboxyalkoxy such as carboxymethoxy, methylsulphanyl, methylsulphinyl, methylsulphonyl or carboxy$C_{3-6}$cycloalkyl, —$(CHR^{21})_r$—$NR^{22}R^{23}$ (where r is 0–2, each $R^{21}$ is independently hydrogen or alkyl, in particular $C_{1-4}$ alkyl, $R^{22}$ and $R^{23}$ are independently selected from H and $C_{1-4}$alkyl or $R^{22}$ and $R^{23}$ together with the nitrogen to which they are attached form a 5 or 6 membered ring optionally containing one further heteroatom selected from O, N, S, S(O) or $SO_2$. Suitably $R^{22}$ and $R^{23}$ together form a heterocylic ring such as morpholino or piperazinyl.

Other such groups $R^3$ include optionally substituted aryl groups, such as optionally substituted phenyl or naphthyl group. Suitable substituents for phenyl groups $R^3$ include one or more groups selected from chlorine, fluorine, methyl, trifluoromethyl, trifluoromethoxy, amino, formyl, phenyl, methoxy, phenoxy or phenyl.

$R^3$ may comprise a range of substituents as listed above, in particular, hydrogen or a small substituent group such as $C_{1-4}$alkyl in particular methyl, or trifluoromethyl, and is preferably hydrogen.

Particularly suitable A-B groups are those of formula (i), (ii), (v) and (ix) as shown above. A further particularly suitable A-B group is that of formula (xi) above.

Particularly preferred compounds of formula (I) are compounds of formula (IA) or (IB):

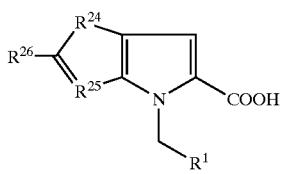

(IA)

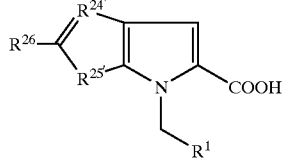

(IB)

or a pharmaceutically acceptable salt, ester of amide thereof, where $R^1$ is as defined above, and is preferably a halo substituted phenyl group such as 3,4-dichlorophenyl, $R^{26}$ is hydrogen or $C_{1-4}$ alkyl, in particular methyl, and in formula (IA)
(i) $R^{24}$ is sulphur and $R^{25}$ is CH; or
(ii) $R^{24}$ is sulphur and $R^{25}$ is nitrogen; or
(iii) $R^{24}$ is oxygen and $R^{25}$ is CH; or
(iv) $R^{24}$ is $NCH_3$ and $R^{25}$ is CH;
and in Formula (IB)
(i) $R^{24'}$ is CH and $R^{25'}$ is sulphur; or
(ii) $R^{24'}$ is CH and $R^{25'}$ is oxygen; or
(iii) $R^{24'}$ is nitrogen and $R^{25'}$ is sulphur.

Particularly preferred examples are compounds of formula (IA) where $R^1$ is a halo substituted phenyl such as 3,4-dichlorophenyl, 3,4-difluorophenyl, 3-fluoro4-chlorophenyl, 3-chloro-4-fluorophenyl, $R^{26}$ is hydrogen or methyl, $R^{24}$ is sulphur and $R^{25}$ is either CH or nitrogen.

Other particular examples are compounds of formula (IA) where $R^1$ is a halo substituted phenyl such as 3,4-dichlorophenyl, 3,4-difluorophenyl, 3-fluoro4-chlorophenyl, 3-chloro-4-fluorophenyl, $R^{24}$ is oxygen, $R^{25}$ is CH, and $R^{26}$ is either hydrogen or methyl.

Yet further preferred examples are compounds of formula (IB) where $R^1$ is a halo substituted phenyl such as 3,4-dichlorophenyl, 3,4-difluorophenyl, 3-fluoro-4-chlorophenyl, 3-chloro-4-fluorophenyl, $R^{25'}$ is sulphur, $R^{26}$ is hydrogen and $R^{24'}$ is either CH or nitrogen.

Preferably the compound of formula (IA) or (IB) is an acid.

Suitable pharmaceutically acceptable salts of compounds of formula (I) include are base salts such as an alkali metal salt for example sodium an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. In another aspect, where the compound is sufficiently basic, suitable salts include acid addition salts such as methanesulfonate, fumarate, hydrochloride, hydrobromide, citrate, maleate and salts formed with phosphoric and sulphuric acid. There may be more than one cation or anion depending on the number of charged functions and the valency of the cations or anions. A preferred pharmaceutically acceptable salt is a sodium salt.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkyl esters such as methyl or ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxy-carbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl;

and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable value for an amide includes, for example, a N—$C_{1-6}$alkyl and N,N-di-($C_{1-6}$alkyl)amide such as N-methyl, N-ethyl, N-propyl, N,N-dimethyl, N-ethyl-N-methyl or N,N-diethylamide.

Particular compounds of formula (I) are listed below in Table I. In the formula, the dotted line indicates the presence of a double bond, which is either between $R^{40}$ and $R^{41}$ or between $R^{41}$ and $R^{42}$ depending upon the nature and the valency of the groups $R^{40}$, $R^{41}$ and $R^{42}$ as would be understood in the art.

TABLE I

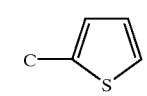

| No. | X | $R^x$ | $R^{40}$ | $R^{41}$ | $R^{42}$ | $R^{43}$ | $R^{44}$ |
|---|---|---|---|---|---|---|---|
| 1 | $CH_2$ | $CH_2CH_3$ | CH | CH | S | Cl | Cl |
| 2 | $CH_2$ | H | CH | CH | S | Cl | Cl |
| 3 | $CH_2$ | $CH_2CH_3$ | O | CH | CH | Cl | Cl |
| 4 | $CH_2$ | H | O | CH | CH | Cl | Cl |
| 5 | $CH_2$ | $CH_2CH_3$ | CH | CH | O | Cl | Cl |
| 6 | $CH_2$ | H | CH | CH | O | Cl | Cl |
| 7 | $CH_2$ | $CH_2CH_3$ | S | CH | CH | Cl | Cl |
| 8 | $CH_2$ | H | S | CH | CH | Cl | Cl |
| 9 | $CH_2$ | $CH_2CH_3$ | S | CBr | CH | Cl | Cl |
| 10 | $CH_2$ | $CH_2CH_3$ | S | 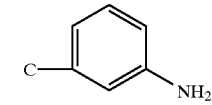 | CH | Cl | Cl |
| 11 | $CH_2$ | $CH_2CH_3$ | S | 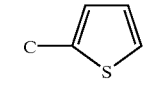 | CH | Cl | Cl |
| 12 | $CH_2$ | H | S | 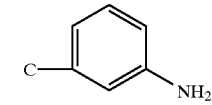 | CH | Cl | Cl |
| 13 | $CH_2$ | H | S | 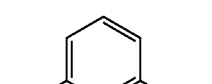 | CH | Cl | Cl |
| 14 | $CH_2$ | H | S | CBr | CH | Cl | Cl |
| 15 | $SO_2$ | $CH_3$ | CH | CH | S | Cl | Cl |
| 16 | $SO_2$ | H | CH | CH | S | Cl | Cl |
| 17 | $CH_2$ | $CH_2CH_3$ | NCH$_3$ | CH | CH | Cl | Cl |
| 18 | $CH_2$ | H | NCH$_3$ | CH | CH | Cl | Cl |
| 19 | $SO_2$ | $CH_3$ | O | CH | CH | Cl | Cl |
| 20 | $SO_2$ | H | O | CH | CH | Cl | Cl |
| 21 | $CH_2$ | $CH_3$ | O | CH | CH | Cl | Cl |
| 22 | $CH_2$ | H | O | $COCH_3$ | CH | Cl | Cl |
| 23 | $CH_2$ | $CH_3$ | CH | CH | S | Cl | Cl |
| 24 | $CH_2$ | $CH_2CH_3$ | O | $CCH_3$ | CH | Cl | Cl |
| 25 | $CH_2$ | H | O | $CCH_3$ | CH | Cl | Cl |
| 26 | $CH_2$ | $CH_2CH_3$ | NCH$_3$ | CH | N | Cl | Cl |

TABLE I-continued

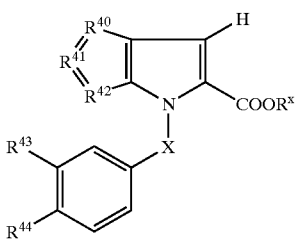

| No. | X | $R^x$ | $R^{40}$ | $R^{41}$ | $R^{42}$ | $R^{43}$ | $R^{44}$ |
|---|---|---|---|---|---|---|---|
| 27 | $CH_2$ | H | $NCH_3$ | CH | N | Cl | Cl |
| 28 | $CH_2$ | $CH_2CH_3$ | N | CH | $NCH_3$ | Cl | Cl |
| 29 | $CH_2$ | H | N | CH | $NCH_3$ | Cl | Cl |
| 30 | $CH_2$ | $CH_2CH_3$ | S | CH | N | Cl | Cl |
| 31 | $CH_2$ | H | S | CH | N | Cl | Cl |
| 32 | $CH_2$ | $CH_2CH_3$ | S | $CCH_3$ | CH | Cl | Cl |
| 33 | $CH_2$ | $CH_2CH_3$ | S | $CCH_3$ | CH | F | F |
| 34 | $CH_2$ | H | S | $CCH_3$ | CH | Cl | Cl |
| 35 | $CH_2$ | H | S | $CCH_3$ | CH | F | F |
| 36 | $CH_2$ | $CH_3$ | O | CCHO | CH | Cl | Cl |
| 37 | $CH_2$ | $CH_3$ | O | $CCH_2OH$ | CH | Cl | Cl |
| 38 | $CH_2$ | H | O | $CCH_2OH$ | CH | Cl | Cl |
| 39 | $CH_2$ | $CH_3$ | O | CCOOH | CH | Cl | Cl |
| 40 | $CH_2$ | H | O | CCOOH | CH | Cl | Cl |
| 41 | $CH_2$ | $CH_3$ | O | C—CN | CH | Cl | Cl |
| 42 | $CH_2$ | H | O | C—CN | CH | Cl | Cl |
| 43 | $CH_2$ | $CH_3$ | O | $C—C(O)NH_2$ | CH | Cl | Cl |
| 44 | $CH_2$ | $CH_3$ | O | C-tetrazol-5-yl | CH | Cl | Cl |
| 45 | $CH_2$ | H | O | C-tetrazol-5-yl | CH | Cl | Cl |
| 46 | $CH_2$ | $CH_3$ | O | $C—CH_2N(CH_3)_2$ | CH | Cl | Cl |
| 47 | $CH_2$ | H | O | $C—CH_2N(CH_3)_2$ | CH | Cl | Cl |
| 48 | $CH_2$ | $CH_3$ | N | CH | S | Cl | Cl |
| 49 | $CH_2$ | $CH_3$ | N | $CCH_3$ | S | Cl | Cl |
| 50 | $CH_2$ | H | N | CH | S | Cl | Cl |
| 51 | $CH_2$ | H | N | $CCH_3$ | S | Cl | Cl |
| 52 | $CH_2$ | $CH_2CH_3$ | S | CH | N | F | F |
| 53 | $CH_2$ | H | S | CH | N | F | F |
| 54 | $CH_2$ | $CH_3$ | O | $CCH_3$ | CH | F | Cl |
| 55 | $CH_2$ | $CH_3$ | O | $CCH_3$ | CH | Cl | F |
| 56 | $CH_2$ | H | O | $CCH_3$ | CH | F | Cl |
| 57 | $CH_2$ | H | O | $CCH_3$ | CH | Cl | F |
| 58 | $CH_2$ | $CH_3$ | O | $COCH_3$ | CH | Cl | Cl |

Of these, the compounds numbered 4, 25, 34, 50 and 56 in Table I are of special interest and these compounds, or a pharmaceutically acceptable salt thereof, are provided as a further feature of the invention.

The invention further provides a compound of formula (I) as defined above for use in the treatment of inflammatory disease.

Furthermore, the invention provides the use of a compound of formula (I) as defined above in the preparation of a medicament for the treatment of inflammatory disease.

Certain compounds of formula I are know, for example particular compounds disclosed in Molecules (1997), 2(4), 69–79, Chem. Pap. (1996), 50(2), 72–76, Chem. Pap. (1994), 48(4), 268–73, Heterocycles (1994), 37(3), 1695–700 and (1989), 29(10), 1943–9, Coll. Czech. Chem. Commun. (1994), 59(2), 473–481 and 499–502, Coll. Czech. Chem. Commun. (1993), 58(9), 2139–49, Coll. Czech. Chem. Comm. (1992), 57(7), 1487–94, Monatsh. Chem. (1992), 123(8–9), 807–15 and Magn. Reson. Chem. (1990), 28(9), 830–1. However, prior to the present invention it was not known that any of these compounds possessed inhibitory activity against MCP-1.

Certain compounds of formula (I) are novel and these form a further aspect of the invention. Thus the invention farther provides a compound of formula (I) as defined above, or a pharmaceutically acceptable salt or in vivo hydrolysable ester thereof. which is an inhibitor of monocyte chemoattractant protein-1; subject to the following provisos: a) that where A-B forms a group of sub-formula (i) or (iv) above, $R^1$ is other than phenyl, amino phenyl or nitrophenyl; and b) that where A-B forms a group of sub-formula (iii) above, $R^{13}$ is methyl and $R^{15}$ is hydrogen, $R^{14}$ is not CHO; c) that where A-B form a group of sub-formula (v) above and X is $SO_2$, $R^1$ is other than unsubstituted phenyl.

Particular and preferred novel compounds of formula (I) are those as described above in relation to the pharmaceutical compositions.

In particular a preferred group of compounds are compounds of formula (IA) and (IB) as defined above.

Some compounds of formula (I) may possess chiral centres. It is to be understood that the invention encompasses all such optical isomers and diastereoisomers of compounds of formula (I) and pharmaceutical compositions containing these.

The invention further relates to all tautomeric forms of the Compounds of formula (I) and pharmaceutical compositions containing these.

It is also to be understood that certain compounds of the formula (I) can exist in solvated as well as unsolvated forms such as, for example, hydrated forms. It is to be understood Compounds of formula (I) are suitably prepared by reacting a compound of formula (VII):

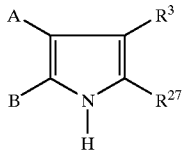

VII where A, B and $R^3$ are as defined in relation to formula (I) and $R^{27}$ is either hydrogen or a group $R^2$ as defined in claim 1; with compound of formula (VIII):

    VIII where $R^1$ and X are as defined in relation to formula (I) and Z is a leaving group; and thereafter if desired or necessary, converting the group $R^{27}$ to a group $R^2$ and/or to a different such group.

Suitable leaving groups for Z include halide such as chloride, bromide or iodide, as well as mesylate or tosylate. The reaction is suitably effected in an organic solvent such as dimethylformamide (DMF) tetrahydrofuran (THF) or DCM in the presence of a base such as sodium hydride, sodium hydroxide, potassium carbonate. Optionally the reaction is effected in the presence of a suitable phase transfer catalyst. The choice of base and solvent is interdependent to a certain extent in that certain solvents are compatible with some bases only as is understood in the art. For example, sodium hydride may preferably be used with dimethylformamide or tetrahydrofuran and sodium hydroxide is preferably used with dichloromethane and a phase transfer catalyst.

The reaction can be carried out at moderate temperatures, for example from 0 to 50° C. and conveniently at about ambient temperature.

Preferably, $R^{27}$ is an ester group in the compound of formula VII and this may be subsequently converted to an acid or amide or to another ester or salt, by conventional methods. For example, when X is a group $SO_2$ and $R^2$ is a methyl ester of carboxy, it may be converted to the corresponding carboxylic acid by reaction with lithium iodide in dry pyridine or DMF.

Alternatively, where $R^{27}$ is hydrogen, it may be converted to for instance a carboxylic acid ester group by reaction with lithium diisopropyl amide (LDA), followed by an alkyl chloroformate. The reaction is suitably effected in an organic solvent such as tetrahydrofuran (THF) at low temperatures for example of from –78 to 0° C., preferably at about –20 to –40° C. In this case, the group on the nitrogen atom is suitably one that will direct metallation to the 2-position, such as phenylsulphonyl.

Compounds of formula (VII) are either known compounds or they may be prepared from known compounds by conventional methods.

For example, compounds of formula (VII) may be prepared by cyclisation of a compound of formula (IX):

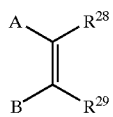

(IX)

where A and B are as defined in relation to formula (I) and $R^{28}$ and $R^{29}$ represent a combination of moieties which can cyclise to form an appropriately substituted pyrrole ring. For example, one of $R^{28}$ and $R^{29}$ can be a group of formula —CH=C($R^{30}$)$N_3$ where $R^{30}$ is a group $R^2$ as defined above, or a protected form thereof, and the other may be hydrogen. Cyclisation to form a compound of formula (VII) may then be effected by heating for example under reflux in an organic solvent, in particular a high boiling aprotic solvent such as xylene or toluene.

Alternatively, one of $R^{28}$ and $R^{29}$ may be nitro and the other may be a group of formula —$CH_2C(O)R^{27}$ where $R^{27}$ is as defined above in relation to formula (VII). These compounds will cyclise in the presence of a catalyst such as palladium on carbon in the presence of hydrogen. The reaction may be effected at moderate temperatures for example of from 0 to 80° C., conveniently at about ambient temperature.

Thus examples of compounds of formula (IX) include compounds of formula (X) and (XI):

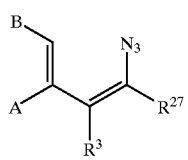

(X)

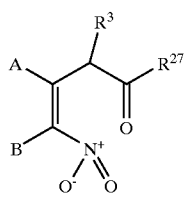

(XI)

Compounds of formula (X) may be prepared for example by reacting a compound of formula (XII):

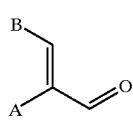

(XII)

with a compound of formula (XIII):

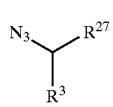

(XIII)

where A, B, $R^3$ and $R^{27}$ are as defined hereinbefore. The reaction may be effected in an organic solvent such as ethanol at low temperatures of from –20 to 0° C., suitably at about 0° C. The reaction is suitably effected in the presence of a base such as an alkoxide, in particular an ethoxide, for example potassium ethoxide.

Compounds of formula (XIII) are suitably prepared by reacting a compound of formula (XIV):

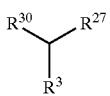

(XIV)

where $R^3$ and $R^{27}$ are as defined above and $R^{30}$ is a leaving group such as halide and in particular bromide, with an azide salt, such as an alkali metal azide salt in particular sodium azide.

Compounds of formula (XI) may be prepared by reacting a compound of formula (XV):

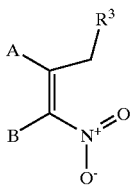

(XV)

where A, B and $R^3$ are as defined above, with a compound of formula (XVI):

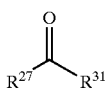

(XVI)

where $R^{27}$ is as defined above and $R^{31}$ leaving group. Examples of compounds of formula (XVI) are oxalates such as diethyloxalate. The reaction is suitably effected in the presence of a base such as sodium hydride in an organic solvent such as THF. Moderate temperatures of from 0 to 40 and conveniently ambient temperature is employed.

Compounds of formulae (XII),(XIV), (XV) and (XVI) are known compounds or they can be prepared from known compounds by conventional methods.

Substituents on the ring formed by A-B may be introduced either during synthesis as outlined above or using various methods which would be apparent to the skilled person depending upon the nature of the particular substituent to be introduced. Alternatively, one substituent may be changed for a different substituent using conventional chemical methods. Other possibilities would be apparent to the skilled person.

Certain of the intermediates defined herein are novel, for example certain compounds of formula (VII), and are provided as a further feature of the invention.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such an peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gun acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol. or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, $30\mu$ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of rats.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

In a further aspect, the invention provides a method of treating inflammatory disease by administering a compound of formula (I) as described above, or a pharmaceutical composition as described above, The invention is farther illustrated, but not limited by the following Examples in which the following general procedures were used unless stated otherwise.

N,N-Dimethylformamide (DMF) was dried over 4 Å molecular sieves. Anhydrous tetrahydrofuran (THF) was obtained from Aldrich SURESEAL™ bottles. Other commercially available reagents and solvents were used without fisher purification unless otherwise seed. Organic solvent extracts were dried over anhydrous $MgSO_4$, $^1H$, $^{13}C$ and $^{19}F$ NMR were recorded on Bruker WM200, WM250, WM300 or WM400 instruments using $Me_2SO$-$d_6$ with $Me_4Si$ or $CCl_3F$ as internal standard as appropriate, unless otherwise sated. Chemical shifts are in d (ppm) and peak multiplicities are designated as follows: s, singlet; d, doublet; dd, doublet of doublets; t, triplet; dt, doublet of triplets; q, quartet; m, multiplet; br, broad. Mass spectra were recorded on VG 12—12 quadrupole, VG 70-250 SE, VG ZAB 2-SE or a VG modified AEI/Kratos MS9 spectrometers. For TLC analysis, Merck precoated TLC plates (silica gel 60 F254, d=0.25 mm) were used. Flash chromatography was performed on silica (Merck Kieselgel: Art.9385). Melting point determinations were performed on a Kofler block or with a Büchi melting point apparatus and are uncorrected. All temperatures are in degrees Centigrade.

PREPARATION 1

Ethyl Azidoacetate

Ethyl bromoacetate (3.43 ml) was added to a suspension of sodium side (3 8) in DMF (50 ml) at ambient temperature and the reaction stirred at 90° C. for 5 hours. The reaction was poured into ice-water (300 g) and extracted with ether. Combined organic extracts were washed with water and brine, dried ($MgSO_4$) and concentrated to give the product as a colorless oil which was used without further purification (3.37 g, 84%), NMR d($CDCl_3$) 1.30 (3H, t), 3.82 (2H, s), 4.23 (2H, q); M/z (+) 130 ($MH^+$).

PREPARATION 2

Methyl Azidoacetate

The procedure described in Example 1 was repeated using the appropriate bromoacetate ester. The title compound was obtained in 82% yield; NMR d($CDCl_3$) 3.80 (3H, s), 3.90 (2H, s).

PREPARATION 3

Ethyl 2-azido-3-(2-thienyl)propenoate

A solution of ethyl azidoacetate (1.38 g) and thiophene-2-carboxaldehyde (1 g) in ethanol (20 ml) was added dropwise to a solution of potassium ethoxide (0.9 g) in ethanol (20 ml) at 0° C. The reaction was stirred for 2 hours at 0° C. and 2 hours at ambient temperature then poured into saturated aqueous ammonium chloride solution (150 ml) and extracted with ether. Combined organic extracts were dried ($MgSO_4$), concentrated in vacuo and the residue purified by column chromatography using isohexane as eluent to give the product as a pale yellow crystalline solid (0.49 g, 25%), NMR d($CDCl_3$) 1.40 (3H, t), 4.37 (2H, q), 7.08 (2H, m), 7.18 (1H, s), 7.38 (1H, m), 7.52 (1H, d).

PREPARATION 4

Ethyl 4H-thieno[3,2-b]pyrrole5-carboxylate

A solution of ethyl 2-azido-3-(2-thienyl)propenoate (0.45 g) in xylene (10 ml) was heated at reflux for 30 minutes, concentrated in vacuo and the residue purified by column chromatography using isohexane-15% ethyl acetate as eluent to give the product as a pale yellow solid (0.26 g, 66%), NMR d($CDCl_3$) 1.40 (3H, t), 4.39 (2H, q), 6.98 (1H, d), 7.18 (1H, s), 7.35 (1H, d), 9.30 (1H, bs) M/z (−) 194 (M-$H^+$), 166.

PREPARATION 5

4-Hydroxymethyl-2-methylthiazole

Lithium aluminium hydride (1M solution in tetrahydrofuran, 140 mL) was added dropwise to a solution of ethyl 2-methylthiazole4-carboxylate (22 g) in tetrahydrofuran at 0° C. The reaction was warmed to ambient temperature, poured into saturated aqueous sodium hydrogencarbonate solution and extracted with ethyl acetate. Combined organic extracts were dried ($MgSO_4$), concentrated and the residue purified by column chromatography using ethyl acetate as eluent to give the product as a yellow gum (10 g, 55%), NMR d($CDCl_3$) 2.7 (3H, s), 4.72 (2H, s), 7.02 (1H, s).

PREPARATION 6

2-Methylthiazole4-carboxaldehyde

Oxalyl chloride (2M solution in dichloromethane, 2.4 mL) was added dropwise to a solution of 4-hydroxymethyl-2-methylthiazole (0.5 g) and dimethylsulphoxide (0.34 mL) in dichloromethane (15 mL) at −60° C. The reaction was warmed to ambient temperature, cooled to −60° C. and N,N-diisopropylamine (2.02 mL) added. Reaction then warmed to ambient temperature, poured into water, and extracted with dichloromethane. Combined organic extracts were dried, concentrated in vacuo and purified by column chromatography using iso-hexane to iso-hexane: 40% ethyl acetate as eluent to yield the product as a pale yellow solid, (0.27 g, 55%), NMR d($CDCl_3$) 2.8 (3H, s), 8.05 (1H, s), 9.98 (1H, s); M/z (+) 128 ($MH^+$).

PREPARATION 7

The procedure described in Preparations 3 and 4 were repeated using the appropriate heteroaryl aldehyde and azidoacetate ester. Thus were obtained the compounds described below.

PREPARATION 7a

Ethyl 4H-thieno[2,3-b]pyrrole-5-carboxylate

15% yield (2 steps), M/z (−) 194 (M-$H^+$), 166, 122.

PREPARATION 7b

Ethyl 4H-furo[3,2-b]pyrrole-5-carboxylate

18% yield (2 steps), M/z (+) 180 ($MH^+$), 152, 134, 108, 102.

PREPARATION 7c

Ethyl 4H-furo[2,3-b]pyrrole-5-carboxylate

9% yield (2 steps), M/z (−) 179 (M-$H^+$), 178, 150, 106.

PREPARATION 7d

Ethyl 4H-1-methylpyrrolo[3,2-b]pyrrole-5carboxylate

7% yield (2 steps), M/z (+) 193 ($MH^+$), 147.

PREPARATION 7e

Methyl 4H-furo[3,2-b]pyrrole-5-carboxylate

25% yield (2 steps), NMR d(DMSO) 3.78 (3H, s), 6.58 (1H, s), 6.72 (1H, s), 7.78 (1H, s), 11.64 (1H, bs); M/z (−) 165 ($M^+$), 164.

PREPARATION 7f

Ethyl 4H-3-bromothieno[3,2-b]pyrrole-5-carboxylate

3% yield (2 steps), NMR d(DMSO) 1.28 (3H, t), 4.24 (2H, q), 7.02 (1H, s), 7.18 (2H, s), 12.15 (1H, bs); M/z (−) 274 ($M^+$), 272.

PREPARATION 7g

Methyl 4H-thieno[2,3-b]pyrrole-5-carboxyulate

7% yield (2 steps), NMR d(DMSO) 3.80 (3H, s), 7.00 (2H, m), 7.10 (1H, d), 12.25 (1H, bs); M/z (−) 180 (M-$H^+$).

PREPARATION 7h

Ethyl 1-methyl-1,4dihydropyrrolo[2,3-d]imidazole-5-carboxylate

24% yield (2 steps), NMR d(DMSO) 1.25 (3H, t), 3.7 (3H, s), 4.2 (2H, q), 6.7 (1H, s), 7.7 (1H, s), 11.6 (1H, bs); M/z (+) 194 ($MH^+$).

PREPARATION 7i

Ethyl 3-methyl-3,4-dihydropyrrolo[2,3-d]imidazole-5carboxylate

7% yield (2 steps), NMR d(DMSO) 1.3 (3H, t), 3.7 (3H, s), 4.2 (2H, q), 6.7 (1 H, s), 7.6 (1H, s), 11.7 (1H, bs); M/z (+) 194 ($MH^+$).

PREPARATION 7j

Ethyl 4H-pyrrolo[2.3-d][1,3]thiazole-5-carboxylate

10% yield (2 steps), NMR d(DMSO) 1.3 (3H, t), 4.3 (2H, q), 7.3 (1H, s), 8.3 (1H, s), 9.2 (1H, bs).

PREPARATION 7k

Ethyl 4H-2-methylthieno[3,2-b]pyrrole-5-carboxylate

67% yield (2 steps), NMR d(DMSO) 1.24 (3H, t), 2.43 (3H, s), 4.23 (2H, q), 6.70 (1H, s), 6.95 (1H, s); M/z (−) 208 (M-$H^+$).

PREPARATION 7l

Methyl 4H-pyrrolo[3,2-d][1,3]thiazole-5-carboxylate

4% yield (2 steps), NMR d(DMSO) 3.82 (3H, s), 7.19 (1H, s), 8.84 (1H, s); M/z (+) 183 (MH$^+$).

PREPARATION 7m

Methyl 2-methyl-4H-pyrrolo[3,2-d][1,3]thiazole-5-carboxylate

38% yield (2 steps), NMR d(DMSO) 2.68 (3H, s), 3.8 (3H, s), 7.05(1H, s); M/z (+) 197 (MH$^+$).

PREPARATION 7n

Methyl 4H-2-methoxyfuro[3,2-b]pyrrole-5-carboxylate

19% yield (2 steps), NMR d(DMSO) 3.7 (1H, s), 3.9 (1H, s), 5.6 (1H, s), 6.65 (1H, s), 11.55 (1H, s); M/z (+) 196 (MH$^+$).

EXAMPLE 1

Ethyl 4-(3,4-dichlorobenzyl)thieno[3,2-b]pyrrole-5-carboxylate (Compound No 7 in Table 1)

Sodium hydride (32 mg, 60%), was added to a solution of ethyl 4H-thieno[3,2-b]pyrrole-5-carboxylate (0.13 g) (from Preparation 4) and the reaction stirred for 30 minutes. 3,4-Dichlorobenzyl bromide (0.22 g) was added and stirring continued for a further 2 hours. The reaction was quenched by addition of water and extracted with ether. Combined organic extracts were dried (MgSO$_4$) and concentrated and the residue purified by column chromatogaphy using isohexane-5% ethyl acetate as eluent to give the product as a yellow solid (0.15 g, 64%), NMR d(DMSO) 1.24 (3H, t), 4.22 (2H, q), 5.73 (2H, s), 6.63 (1H, d), 6.98 (1H, dd), 7.25 (2H, m), 7.37 (1H, s), 7.55 (1H, d); M/z (+) 354 (M$^+$), 214, 158, 129.

EXAMPLE 2

The procedure described in Example 1 was repeated using the appropriate pyrrole and benzyl halide or arylsulfonyl chloride. Thus were obtained the compounds described below.

EXAMPLE 2a

Ethyl 4-(3,4-dichlorobenzyl)thieno[2,3-b]pyrrole-5-carboxylate (Compound No.1 in Table 1)

73% yield, NMR d(CDCl$_3$) 1.36 (3H, t), 4.30 (2H, q), 5.62 (2H, s), 6.91 (1H, d), 7.02 (1H, d), 7.07 (1H, dd), 7.24 (1H, s), 7.35 (2H, m); M/z (+) 354 (M$^+$), 319.

EXAMPLE 2b

Ethyl 4-(3,4-dichlorobenzyl)furo[3,2-b]pyrrole-5-carboxylate (Compound No.3 in Table 1)

52% yield, NMR d(CDCl$_3$) 1.35 (3H, t), 4.26 (2H, q), 5.60 (2H, s), 6.28 (1H, d), 6.89 (1H, s), 6.96 (1H, dd), 7.23 (1H, s), 7.36 (1H, d), 7.50 (1H, d); M/z (+) 338 (M$^+$).

EXAMPLE 2c

Ethyl 4-(3,4-dichlorobenzyl)furo[2,3-b]pyrrole-5-carboxylate (Compound No. 5 in Table 1)

88% yield, NMR d(CDCl$_3$) 1.34 (3H, t), 4.28 (2H, q), 5.60 (2H, s), 6.53 (1H, d), 6.96 (1H, s), 7.09 (1H, dd), 7.30 (1H, d), 7.37 (2H, m); M/z (+) 338 (M$^+$).

EXAMPLE 2d

Ethyl 4-(3,4-dichlorobenzyl)-1-methylpyrrolo([3,2-b]pyrrole-5-carboxylate (Compound No. 17 in Table 1)

81% yield, NMR d(CDCl$_3$) 1.33 (3H, t), 3.67 (3H, s), 4.24 (2H, q), 5.58 (2H, s), 5.80 (1H, d), 6.79 (1H, d), 6.84 (1H, s), 6.97 (1H, dd), 7.24 (1H, m), 7.32 (1H, d); M/z (+) 351 (M$^+$).

EXAMPLE 2e

Methyl 4-(3,4-dichlorobenzenesulfonyl)furo[3,2-b]pyrrole-5-carboxylate (Compound 19 in Table 1)

70% yield. NMR d(DMSO) 3.72 (3H, s), 7.03 (1H, s), 7.38 (1H, s), 7.96 (2H, m), 8.06 (1H, s), 8.23 (1H, s); M/z (+) 374 (M$^+$), 344, 165, 121.

EXAMPLE 2f

Methyl 4-(3,4-dichlorobenzyl)furo[3,2-b]pyrrole-5-carboxylate (Compound 21 in Table I)

65% yield, NMR d(DMSO) 3.72 (3H, s), 5.63 (2H, s), 6.80 (1H, d), 6.90 (1H, s), 7.02 (1H, dd), 7.39 (1H, s), 7.55 (1H, d), 7.80 (1H, d); M/z (+) 324 (M$^+$) 259, 243, 158, 121.

EXAMPLE 2g

Methyl 4-(3,4-dichlorobenzenesulfonyl)thieno[2,3-b]pyrrole-5-carboxylate (Compound 15 in Table I)

70% yield, NMR d(DMSO) 3.70 (3H, s), 7.17 (2H, d), 7.46 (1H, d), 7.47 (1H, s), 7.84 (1H, dd), 7.93 (1H, d), 8.20 (1H, s); M/z (+) 392 (M$^+$), 390, 360, 339, 159, 150, 115.

EXAMPLE 2h

Ethyl 4-(3,4-dichlorobenzyl)-2-bromothieno[3.2-b]pyrrole-5-carboxylate (Compound 9 in Table I)

62% yield, NMR d(DMSO) 1.22 (3H, t), 4.20 (2H, q), 5.66 (2H, s), 6.96 (1H, dd), 7.21 (1H, s), 7.38 (1H, m), 7.57 (1H, d), 7.59 (1H, s); M/z (+)434 (M$^+$), 119.

EXAMPLE 2i

Ethyl 4-(3,4-dichlorobenzyl)-2-methylfuro[3.2-b]pyrrole-5-carboxylate (Compound 24 in Table I)

The title compound was prepared from ethyl 2-methylfuro[3,2-b]pyrrole-5-carboxylate in 74% yield, NMR d(DMSO) 1.20 (3H, t), 2.35 (3H, s), 4.20 (2H, q), 5.60 (2H, s), 6.4 (1H, s), 6.80 (1H, s), 7.00(1H, m), 7.40 (1H, s), 7.60 (1H, d).

EXAMPLE 2j

Ethyl 4-(3,4-dichlorobenzyl)-1-methyl-1,4-dihydropyrrolo[2,3-d]imidazole-5-carboxylate (Compound No 26 in Table I)

70% yield, NMR d(DMSO) 1.2 (3H, t), 3.7 (3H, s), 4.2 (2H, q), 5.6 (2H, s), 6.9 (1H, s), 7.05 (1H, m), 7.35 (1H, m), 7.5 (1H, d), 7.8 (1H, s); M/z (+) 352 (MH$^+$).

EXAMPLE 2k

Ethyl 4-(3,4-dichlorobenzyl)-3-methyl-3,4-dihydropyrrolo[2,3-d]imidazole-5-carboxylate (Compound No 28 in Table I)

79% yield, NMR d(DMSO) 1.25 (3H, t), 3.6 (3H, s), 4.2 (2H, q), 5.8 (2H, s), 6.85 (1H, m), 7.0 (1H, s), 7.3 (1H, s), 7.6 (2H, m); M/z (+) 352(MH$^+$).

EXAMPLE 2l

Ethyl 4-(3,4-dichlorobenzyl)-4-H-pyrrolo[2,3-d][1,3]thiazole-5-carboxylate (Compound No 30 in Table I)

100% yield, NMR d(DMSO) 1.2 (3H, t), 4.25 (2H, q), 5.8 (2H, s), 7.0 (1H, m), 7.3 (1H, s), 7.4 (1H, m), 7.55 (1H, d), 9.15 (1H, s); M/z (+) 355(MH$^+$).

EXAMPLE 2m

Ethyl 4-(3,4dichlorobenzyl)-2-methylthieno[3,2-b]pyrrole-5-carboxylate (Compound No 32 in Table I)

94% yield, NMR d(CDCl$_3$) 1.35 (3H, t), 2.55 (3H, s), 4.26 (2H, q), 5.60 (2H, s), 6.56 (1H, s), 6.90 (1H, dd), 7.20 (2H, m), 7.35 (1H, d); M/z (+) 370, 368 (M$^+$).

EXAMPLE 2n

Ethyl 4-(3,4-difluorobenzyl)-2-methylthieno[3,2-b]pyrrole-5-carboxylate (Compound No 33 in Table I)

64% yield, NMR d(CDCl$_3$) 1.35 (3H, t), 2.55 (3H, s), 4.30 (2H, q), 5.60 (2H, s), 6.55 (1H, s), 6.80–7.20 (4H, m); M/z (4) 336 (MH$^+$).

EXAMPLE 2o

Methyl 4-(3,4-dichlorobenzyl)-4H-pyrrolo[3,2-d][1,3]thiazole-5-carboxylate (Compound No. 48 in Table I)

58% yield, NMR d(CDCl$_3$) 3.88 (3H, s), 5.68 (2H, s), 7.05 (1H, dd), 7.31 (1H, d), 7.39 (1H, d), 7.45 (1H, s), 8.51 (1H, s); M/z (+) 341 (MH$^+$).

EXAMPLE 2p

Methyl 4-(3,4-dichlorobenzyl)-2-methyl-4H-pyrrolo[3,2-d][1,3]thiazole-5-carboxylate (Compound No 49 in Table I)0

80% yield, NMR d(CDCl$_3$) 2.72 (3H, s), 3.85 (3H, s), 5.62 (2H, s), 7.05 (1H, dd), 7.28 (1H, s), 7.3 (1H, d), 7.39 (1H, d); M/z (+)355 (MH$^+$).

EXAMPLE 2q

Ethyl 4-(3,4-difluorobenzyl)pyrrolo[2,3d][1,3]thiazole5-carboxylate (Compound No. 52 in Table I)

88% yield, NMR d(DMSO) 1.25 (3H, t), 4.25 (2H, q), 5.8 (2H, s), 6.9 (2H, m), 7.2 (1H, m), 7.3 (1H, m), 9.2 (1H, s); M/z (+) 323 (MH$^+$).

EXAMPLE 2r

Methyl 4-(4-chloro-3-fluorobenzyl)-2-metkylfuro[3,2-b]pyrrole-5-carboxylate (Compound No 54 in Table I)

95% yield, NMR d(DMSO) 2.35 (3H, s), 3.7 (3H, s), 5.6 (2H, s), 6.4 (1H, s), 6.85 (1H, s), 6.9 (1H, m), 7.15 (1H, d), 7.5 (1H, t); M/z (+) 322 (MH$^+$).

EXAMPLE 2s

Methyl 4-(3-chloro-4-fluorobenzyl)-2-methylfuro[3,2-b]pyrrole-5-carboxylate (Compound No 55 in Table I)

78% yield, NMR d(DMSO) 2.35 (3H, s), 3.7 (3H, s), 5.55 (2H, s), 6.4 (1H, s), 6.8 (1H, s), 7.1 (1H, m), 7.35 (2H, m): M/z (+) 322 (MM$^+$).

EXAMPLE 2t

Methyl 4-(3,4-dichlorobenzyl)-2-methoxyfuro[3,2-b]pyrrole-5-carboxylate (Compound No 58 in Table I)

47%, NMR d(DMSO) 3.65 (3H, s), 3.90 (3H, s), 5.6 (2H, s), 5.85 (1H, s), 6.85 (1H, s), 7.05 (1H, d), 7.4 (1H, m), 7.6 (1H, d); M/z (+) 354 (MH$^+$).

EXAMPLE 3

Ethyl 4-(3,4-dichlorobenzyl)-2-(thien-2-yl)thieno[3,2-b]pyrrole-5-carboxylate (Compound 10 in Table I)

Tetrakis-(triphenylphosphine)palladium (0) (20 mg) was added to a degassed solution of ethyl4-(3,4-dichlorobenzyl)-2-bromothieno[3,2-b]pyrrole-5-carboxylate (0.1 g) and thiophene-2-boronic acid (34 mg) in ethanol (1 ml), toluene (1 ml) and aqueous potassium carbonate (2N, 1 ml), and the reaction stirred at 80° C. under an argon atmosphere for 6 hours. The reaction was cooled, poured into 2N HCl and extracted with ether. Combined organic extracts were cried (MgSO$_4$), concentrated in vacuo and the residue purified by column chromatography using isohexane to isohexane-25% ethyl acetate as eluent to give the product as a pale yellow crystalline solid (77 mg, 77%), M/z (+) 435 (MH$^+$), 276, 204, 159, 127.

EXAMPLE 4

Ethyl 2-(3-aminophenyl)-4-(3,4-dichlorobenzyl)thieno[3,2-b]pyrrole-5-carboxylate (Compound 11 in Table 1)

The procedure described in Example 3 was repeated using the appropriate boronic acid. The title compound was obtained in 82% yield, M/z (+) 444 (MH$^+$), 285, 241, 213, 186, 179, 159, 123.

EXAMPLE 5

Methyl 4-(3,4-dichlorobenzyl)-2-formylfuro[3,2-b]pyrrole-carboxylate (Compound No 36 in Table 1)

Phosphoryl chloride (1.41 mL) was added to cooled DMF (4.7 mL) and the reaction stirred for 20 min. Methyl 4-(3,4-dichlorobenzyl)furo[3,2-b]pyrrole-5-carboxylate (4.89 g) was added portionwise, keeping the temperature below 10° C. The mixture was stirred for 30 min at this temperature, then heated to 60° C. for 1 hour. The reaction was quenched by pouring into ice/water, neutralised with saturated aqueous sodium hydrogen carbonate solution and extracted with ethyl acetate. The organic extracts were dried (MgSO$_4$), concentrated in vacuo and the residue purified by column chromatography, using iso-hexane: 30% ethyl acetate, increasing to iso-hexane: 70% ethyl acetate to give a pale brown solid (3.85 g, 7%). NMR d(CDCl$_3$) 3.9 (3H, s), 5.65 (2H, s), 6.9 (1H, s), 7.0 (2H, m), 7.25 (1H, s), 9.65 (1H, s); M/z (+) 354 (MH$^+$), 352.

EXAMPLE 6

Methyl 4-(3,4-dichlorobenzyl)-2-hydroxymethylfuro[3,2-b]pyrrole-5-carboxylate (Compound No 37 in Table 1)

Methyl 4-(3,4-dichlorobenzyl)-2-formylfuro[3,2-b]pyrrole-5-carboxylate (0.2 g) was dissolved in methanol (10 mL) and THF (10 mL) and cooled to 0° C. Sodium borohydride (26 mg) was added and the reaction stirred for 2 hours. The mixture was acidified with 2M HCl, partially evaporated, and extracted with ethyl acetate. Combined organic extracts were dried (MgSO$_4$) and concentrated in vacuo to give a white solid (0.23 g), NMR d(CDCl$_3$) 3.8 (3H, s), 4.65 (2H, d), 5.6 (2H, s), 6.2 (1H, s), 6.85 (1H, s), 7.0 (1H, dd), 7.2 (1H, d), 7.35 (1H, d); M/z (+) 340 (MH$^+$), 332, 278.

EXAMPLE 7

Methyl 2-carboxy-4-(3,4-dichlorobenzyl)furo[3,2-b]pyrrole-5-carboxylate (Compound 39 in Table 1)

Methyl 4-(3,4-dichlorobenzyl)-2-formylfuro[3,2-b]pyrrole-5-carboxylate (0.2 g) was dissolved in t-butanol (20 mL) and 2-methylbut-2-ene (10 mL). To this was added dropwise a solution of sodium chlorite (0.46 g) and sodium dihydrogen orthophosphate (0.62 g) in water (10 mL) and the reaction stirred for 18 hours at room temperature. The mixture was partially evaporated and partitioned between ethyl acetate/water. Combined organic extracts were dried (MgSO$_4$) and concentrated in vacuo to give a white solid (0.19 g, 91%), NMR d(DMSO) 3.75 (3H, s), 5.65 (2H, s), 7.0 (1H, s), 7.1 (1H, dd), 7.5 (1H, d), 7.55 (2H, m); M/z (+) 370 (MH$^+$), 368.

EXAMPLE 8

Methyl 2-cyano-4-(3,4-dichlorobenzyl)furo[3,2-b]pyrrole-5-carboxylate (Compound No. 41 Table 1)

Methyl 4-(3,4-dichlorobenzyl)-2-formylfuro[3,2-b]pyrrole-5-carboxylate (0.7 g) was dissolved in pyridine (7 mL). To this was added hydroxyammonium chloride (0.23 g) and reaction heated at 90° C. for 30 min. Acetic anhydride (2.5 mL) was added dropwise and reaction heated at 90° C. for a further 2 hours. The reaction was quenched by pouring onto ice/water, and the resulting precipitate was filtered off and dried in vacuo to give a pale brown solid (0.69 g, 100%), NMR d(CDCl$_3$) 3.85 (3H, s), 5.6 (2H, s), 6.85 (2H, d), 6.95 (1H, dd), 7.2 (1H, d), 7.4 (1H, d); M/z (−) 349 (M-H$^+$), 347, 189.

EXAMPLE 9

Methyl 2-Carboxamido-4-(3,4-dichlorobenzyl)furo[3,2-b]pyrrole-5carboxylate (Compound No 43 in Table I)

2-Cyano-4-(3,4-dichlorobenzyl)furo[3,2-b]pyrrole-5-carboxylate (0.35 g) was dissolved in THF (5mL) and methanol (2.5 mL). To this was added 2M NaOH solution (5 mL) and the reaction was stirred for 18 hours. The solvents were evaporated, the residue dissolved in water, and acidified with acetic acid. The resulting precipitate was filtered and dried in vacuo to give a white solid (333 mg, 99%), NMR d(DMSO) 5.75 (2H, s), 6.65 (1H, s), 7.1 (1H, dd), 7.25 (1H, d), 7.5 (2H, d); M/z (+) 355 (MH$^+$), 353.

EXAMPLE 10

Methyl 4-(3,4-dichlorobenzyl)-2 -(5'-tetrazolyl)furo[3,2-b]pyrrole-5-carboxylate (Compound No 44 in Table 1)

Methyl 2-cyano-4-(3,4-dichlorobenzyl)furo[3,2-b]pyrrole-5-carboxylate (0.35 g) was dissolved in DMF (7.5 mL). To this was added ammonium chloride (64 mg) and sodium azide (78 mg) and the reaction heated at 100° C. for 4 hours. Water was added and the reaction mixture acidified with 2M HCl solution. The resulting precipitate was filtered and dried in vacuo to give a pale brown solid (0.35 g, 89%), NMR d(DMSO) 3.8 (3H, s), 5.7 (2H, s), 7.05 (1H, s), 7.1 (1H, dd), 7.5 (1H, d), 7.6 (2H, m), 7.9 (1H, s); M/z (−) 392 (M-H$^+$), 390, 334.

EXAMPLE 11

Methyl 4-(3,4-dichlorobenzyl)-2-dimethylaminomethylfuro[3,2-b]pyrrole-5-carboxylate (Compound No. 46 in Table 1)

Methyl 4-(3,4-dichlorobenzyl)-2-formylfuro[3,2-b]pyrrole-5-carboxylate (0.25 g) was dissolved in methanol (5 mL) and THF (10 mL), and to this was added sodium acetate (116 mg) and a portion of MgSO$_4$, followed by dimethylamine solution (2M in methanol, 0.53 mL). After 1 hour, a further 2.5 ml dimethylamine solution was added, followed after 30 min by sodium cyanoborohydride (0.45 g). The reaction was stirred for 18 hours and then quenched by addition of 1M potassium carbonate solution, and extracted with ethyl acetate. Combined organic extracts were dried (MgSO$_4$) and concentrated in vacuo. The residue was purified by column chromatography using ethyl acetate increasing to 10% methanol: ethyl acetate as eluent to give a yellow oil (0.15 g, 55%), NMR d(CDCl$_3$) 2.3 (6H, s), 3.5 (2H, s), 3.8 (3H, s), 5.55 (2H, s), 6.15 (1H, s), 6.85 (1H, s), 6.95 (2H, dd), 7.2 (1H, d), 7.35 (1H, d). M/z (+) 383 (MH$^+$), 381, 338, 336.

EXAMPLE 12

4-(3,4-Dichlorobenzyl)thieno[3,2-b]pyrrole-5-carboxylic acid (Compound No. 8 in Table I)

Sodium hydroxide (3N, 1.3 ml) was added to a stirred solution of ethyl 4-(3,4-dichlorobenzyl)thieno[3,2-b]pyrrole-5-carboxylate (0.137 g) in THF (2.5 ml) and methanol (2.5 ml). Stirring was continued for 16 hours at ambient temperature, concentrated in vacuo and the residue dissolved in water. Dropwise addition of acetic acid led to precipitation of the product as a white solid which was filtered and dried (0.107 g, 85%), NMR d(DMSO) 5.79 (2H, s), 7.05 (1H, m), 7.28 (2H, m), 7.42 (1H, s), 7.60 (2H, m); M/z (−) 326 (M$^+$), 324, 282, 280.

EXAMPLE 13

The procedure described in Example 12 was repeated using the appropriate N-benzylpyrrole carboxylic ester. Thus was obtained the compound described below.

EXAMPLE 13a 4-(3,4-Dichlorobenzyl)thieno[2,3-b]pyrrole-5-carboxylic acid (Compound No 2 in Table 1)

84% yield, M/z (−) 326 (M$^+$), 324, 280.

EXAMPLE 13b 4-(3,4-Dichlorobenzyl)furo[3,2-b]pyrrole-5-carboxylic acid (Compound No. 4 in Table I)

78% yield, M/z (−) 310 (M$^+$) 308.

EXAMPLE 13c 4-(3,4-Dichlorobenzyl)furo[2,3-b]pyrrole-5-carboxylic acid (Compound No 6 in Table 1)

55% yield, M/z (−) 310 (M$^+$), 308.

EXAMPLE 13d 4-(3,4-Dichlorobenzyl)-1-methylpyrrolo[3,2-b]pyrrole-5-carboxylic acid (Compound 18 in Table I)

19% yield, M/z (−) 323 (M$^+$), 321.

EXAMPLE 13e 4-(3,4-Dichlorobenzyl)-2-bromothieno[3.2-b]pyrrole-5-carboxylic acid (Compound No. 25 14 in Table I)

70% yield, NMR d(DMSO) 5.72 (2H, s), 7.00 (1H, m), 7.20 (1H, s), 7.42 (1H, s), 7.60 (2H, m), 12.71 (1H, bs); M/z (−) 404 (M-H$^+$), 360, 137. Analysis for $C_{14}H_8BrCl_2NO_2S$ found C, 41.6%; H, 2.1%; N, 3.2%; theory C, 41.5%; H, 2.0%; N, 3.46%.

EXAMPLE 13f 4-(3,4-Dichlorobenzyl)-2-(thien-2-yl)thieno[3,2-b]pyrrole-5-carboxylic acid (Compound No 12 in Table I)

91% yield, M/z (−) 406 (M-H$^+$), 362.

EXAMPLE 13g 2-(3-Aminophenyl)-4-(3,4-dichlorobenzyl)thieno[3,2-b]pyrrole-5-carboxylic acid (Compound No. 13 in Table 1)

76% yield, M/z (−) 415 (M-H$^+$), 371.

EXAMPLE 13h 4-(3,4-Dichlorobenzyl)-2-methylfuro[3,2b]pyrrole-5-carboxylic acid (Compound No. 25 in Table I)

88% yield, M/z (−) 322 (M-H$^+$), 280.

EXAMPLE 13i 4-(3,4-Dichlorobenzyl)-1-methyl-1,4-dihydropyrrolo[2,3-d]imidazole-5-carboxylic acid (Compound No 27 in Table I)

89% yield, NMR d(DMSO) 3.7 (3H, s), 5.6 (2H, s), 6.75 (1H, s), 7.1 (1H, d), 7.35 (1H, m), 7.5 (1H, d), 7.7 (1H, s); M/z (−) 322 (M-H$^+$).

EXAMPLE 13j 4-(3,4-Dichlorobenzyl)-3-methyl-3,4-dihydropyrrolo[2,3-d]imidazole-5-carboxylic acid (Compound No 29 in Table I)

28% yield, M/z (−) 322 (M-H$^+$).

EXAMPLE 13k 4-(3,4-Dichlorobenzyl)-4-H-pyrrolo[2,3-d][1,3]thiazole-5-carboxylic acid (Compound No. 31 in Table I)

70% yield, NMR D(DMSO) 5.6 (2H, s), 7.05 (1H, m), 7.2 (1H, s), 7.4 (1H, m), 7.5 (1H, d), 9.1 (1H, s); M/z (−) 325 (M-H$^+$).

EXAMPLE 13l 4-(3,4Dichlorobenzyl)-2-methylthieno[3,2-b]pyrrole-5-carboxylic acid (Compound No 34 in Table I)

38% yield, NMR d(DMSO) 2.45 (3H, s), 5.65 (2H, s), 6.95 (1H, s), 7.00 (2H, m), 7.38 (1H, d), 7.50 (1H, d); M/z (−) 340 (M$^+$), 338.

EXAMPLE 13m 4-(3,4-Difluorobenzyl)-2-methylthieno[3,2-b]pyrrole-5-carboxylic acid (Compound No 35 in Table 1)

64% yield, NMR d(DMSO) 2.45 (3H, s), 5.65 (2H, s), 6.90 (1H, m), 6.95 (1H, s), 7.16 (1H, s), 7.19 (1H, m), 7.32 (1H, dt); M/z (−) 306 (M-H$^+$).

EXAMPLE 13n 4-(3,4-Dichlorobenzyl)-2-hydroxymethylfuro[3,2-b]pyrrole-5carboxylic acid (Compound No 3A n Table 1)

32% yield, NMR d(DMSO) 4.4 (2H, s), 5.65 (2H, s), 6.55 (1H, s), 6.8 (1H, s), 7.1 (1H, dd), 7.4 (1H, d), 7.55 (1H, d). M/z (+) 342 (MH$^+$), 340, 322.

EXAMPLE 13o 4-(3,4-Dichlorobenzyl)furo[3,2-b]pyrrole-2,5-dicarboxylic acid (Compound No. 40 in Table I)

72% yield, NMR d(DMSO) 5.65 (2H, s), 6.9 (1H, s), 7.1 (1H, dd), 7.5 (3H, m); M/z (+) 354 (MH$^+$), 159, 141.

EXAMPLE 13p 4-(3,4-Dichlorobenzyl)-2-(5'-tetrazolyl)furo[3,2-b]pyrrole-5-carboxylic acid (Compound 45 in Table I)

83% yield, NMR d(DMSO) 5.7 (2H, s), 6.95 (1H, s), 7.1 (1H, dd), 7.5 (2H, m), 7.55 (1H, d); M/z (+) 380(MH$^+$), 378.

EXAMPLE 13q 4-(3,4-Dichlorobenzyl)-2-dimethylaminomethylfuro[3,2-b]pyrrole-5-carboxylic acid (Compound No 47 in Table I)

52% yield, NMR d(DMSO) 2.15 (6H, s), 3.5 (2H, s), 5.6 (2H, s), 6.6 (1H, s), 6.8 (1H, s), 7.1 (1H, dd), 7.4 (1H, d), 7.6 (1H, d); M/z (−) 367 (M-H$^+$), 365, 321.

EXAMPLE 13r 4-(3,4-dichlorobenzyl)-4H-pyrrolo[3,2-d][1,3]thiazole-5-carboxylic acid (Compound No 50 in Table 1)

68% yield, NMR d(DMSO) 5.75 (2H, s), 7.1 (1H, dd), 7.3 (1H, s), 7.48 (1H, d), 7.6 (1H, d), 8.8 (1H, s); M/z (−) 325 (M-H$^+$).

EXAMPLE 13s 4-(3,4-dichlorobenzyl)-2-methyl-4H-pyrrolo[3,2-d][1,3]thiazole-5-carboxylate (Compound No. 51 in Table 1)

79% yield, NMR d(DMSO) 2.64 (3H, s), 5.7 (2H, s), 7.08 (1H, dd), 7.15 (1H, s), 7.45 (1H, d), 7.6 (1H, d); M/z (−) 339 (M-H$^+$).

EXAMPLE 13t 4-(3,4-Difluorobenzyl)pyrrolo[2,3-d][1,3]thiazole-5-carboxylic acid (Compound No.53 in Table I)

70% yield, NMR d(DMSO) 5.8 (2H, s), 6.95 (1H, m), 7.3 (3H, m), 9.1 (1H, s); M/z (−) 293 (M-H$^+$).

EXAMPLE 13u 4-(4-Chloro-3-fluorobenzyl)-2-methylfuro[3,2-b]
pyrrole-5-carboxylic acid (Compound No 56 in
Table I)

77% yield, NMR d(DMSO) 2.35 (3H, s), 5.6 (2H, s), 6.4 (1H, s), 6.75 (1H, s), 6.9 (1H, d), 7.15 (1H, d), 7.5 (1H, t); M/z (−) 306 (M-H$^+$).

EXAMPLE 13v 4-(3-Chloro-4-fluorobenzyl)-2-methylfuro[3,2-b]
pyrrole-5-carboxylic acid (Compound No 57 in
Table I)

71% yield, NMR d(DMSO) 2.35 (3H, s), 5.6 (2H, s), 6.4 (1H, s), 6.75 (1H, s), 7.1 (1H, m), 7.3 (2H, m); M/z (−) 306 (M-H$^+$).

EXAMPLE 13w 4-(3,4-Dichlorobenzyl)-2-methoxyfuro[3,2-b]
pyrrole-5-carboxylic acid (Compound No. 22 in
Table I)

68%), NMR d(DMSO) 3.9 (3H, s), 5.6 (3H, s), 5.8 (1H, s), 6.75 (1H, s), 7.05 (1H, d), 7.4 (1H, s), 7.6 (1H, d); M/z (−) 338 (M-H$^+$).

EXAMPLE 14

4-(3,4-Dichlorobenzenesulfonyl)furo[3,2-b]pyrrole-
5-carboxylic acid (Compound No. 20 in Table I)

Methyl 4-(3,4-dichlorobenzenesulfonyl)furo[3,2-b]pyrrole-5-carboxylate (1.15 g) and lithium iodide (4.0 g) were dissolved in pyridine (50 ml) and heated at reflux for 5 hours, cooled, then concentrated in vacuo. The residue was partitioned between 2N HCl and ether. Combined organic extracts were dried (MgSO$_4$), concentrated, and the residue triturated with ether to give the product as a white crystalline solid which was filtered and dried (0.58 g, 52%), NMR d(DMSO) 7.02 (1H, d), 7.27 (1H, s), 7.88 (2H, s), 8.03 (1H, d), 8.22 (1H, s); M/z (−) 360 (M$^+$), 314, 252, 250, 227, 225, 209, 170. Analysis for $C_{13}H_7Cl_2NO_5S$ found C, 43.2%; H, 2.1%; N, 3.8%; theory C, 41.4%; H, 2.0%; N, 3.9%.

EXAMPLE 15

The procedure described in Example 14 was repeated using the appropriate methyl carboxylic ester. Thus were obtained the compounds described below.

EXAMPLE 15a 4-(3,4-Dichlorobenzenesulfonyl)thieno[2,3-b]
pyrrole-5-carboxylic acid (Compound No. 16 in
Table I)

11% yield, NMR d(DMSO) 7.12 (1H, d), 7.38 (1H, s), 7.42 (1H, d), 7.80 (1H, dd), 7.90 (1H, d), 8.20 (1H, s); M/z (+)378 (M$^+$), 376, 196, 166, 131, 119, 113.

EXAMPLE 15b

2-Cyano-4-(3,4-dichlorobenzyl)furo[3,2-b]pyrrole-5-
carboxylic acid (Compound No 42 in Table I)

81% yield, NMR d(DMSO) 5.65 (2H, s), 6.9 (1H, s), 7.05(1H, dd), 7.45 (1H, d), 7.6 (1H, d), 7.9 (1H, s). M/z (−) 335 (M-H$^+$), 333, 291, 289, 262.

EXAMPLE 16

Biological Assays for hMCP-1 Antagonists
a) hMCP-1 Receptor-binding Assay
  i) Clonning and expression of hMCP-1receptor The MCP-1 receptor B (CCR$^2$B) cDNA was cloned by PCR from THP-1 cell RNA using suitable oligonucleotide primers based on the published MCP-1 receptor sequences (Charo et al., 1994, *Proc. Natl. Acad Sci. USA*, 91, 2752). The resulting PCR products were cloned into vector PCR-II™ (InVitrogen, San Diego, Calif.). Error free CCR2B cDNA was subcloned as a Hind III-Not I fragment into the eukaryotic expression vector pCDNA3 (InVitrogen) to generate pCDNA3/CC-CKR2A and pCDNA3/CCR2B respectively.

Linearised pCDNA3/CCR2B DNA was transfected into CHO-K1 cells by calcium phosphate precipitation (Wigler et al., 1979, *Cell*, 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.*, 6, 134). CHO-K1 clone 7 (CHO-CCR$^2$B) was identified as the highest MCP-1 receptor B expressor.

ii) Preparation of membrane fragments

CHO-CCR2B cells were grown in DMEM supplemented with 10% foetal calf serum, 2 mM glutamine, 1× Non-Essential Amino Acids, 1× Hypoxanthine and Thymidine Supplement and Penicillin-Streptomycin (at 50 μg streptomycin/ml, Gibco BRL). Membrane fragments were prepared using cell lysis/differential centrifugation methods as described previously (Siciliano et al., 1990, *J. Biol. Chem.*, 265, 19658). Protein concentration was estimated by BCA protein assay (Pierce, Rockford, Ill.) according to the manufacturer's instructions.

iii) Assay $^{125}$I MCP-1 was prepared using Bolton and Hunter conjugation (Bolton et al., 1973, *Biochem. J.*, 133, 529; Amersham International plc]. Equilibrium binding assays were carried out using the method of Ernst et al., 1994, *J. Immunol.*, 152, 3541. Briefly, varying amounts of $^{125}$I-labeled MCP-1 were added to 10 mg of purified CHO-CCR2B cell membranes in 100 ml of Binding Buffer. After 1 hour incubation at room temperature the binding reaction mixtures were filtered and washed 5 times through a plate washer (Packard Harvester Filtermate™ 196). Scintillation fluid (25 μl, Microscint™-20, a high efficiency liquid scintillation counting cocktail for aqueous samples) was added to each well and the plate was covered with plate sealer and counted (Packard Top Count™). Cold competition studies were performed as above using 100 pM $^{125}$I-labeled MCP-1 in the presence of varying concentrations of unlabelled MCP-1. Non-specific binding was determined by the inclusion of a 200-fold molar excess of unlabelled MCP-1 in the reaction.

Ligand binding studies with membrane fragments prepared from CHO-CCR2B cells showed that the CCR2B was present at a concentration of 0.2 pmoles/mg of membrane protein and bound MCP-1 selectively and with high affinity (IC$_{50}$=110 pM, K$_d$=120 pM). Binding to these membranes was completely reversible and reached equilibrium after 45 minutes at room temperature, and there was a linear relationship between MCP-1 binding and CHO-CCR2B cell membrane concentration when using MCP-1 at concentrations between 100 pM and 500 pM.

Test compounds dissolved in DMSO (5 μl) were tested in competition with 100 pM labelled MCP-1 over a concentration range (0.1–200 μM) in duplicate using eight point dose-response curves and IC$_{50}$ concentrations were calculated.

Compounds tested of the present invention had $IC_{50}$ values of 50 μM or less in the hMCP-1 receptor binding assay described herein. For example the compound of example 13 g had an $IC_{50}$ of 8.3 μM.

b) MCP-1 Mediated Calcium Flux in THP-1 Cells

The human monocytic cell line THP-1 was grown in a synthetic cell culture medium RPMI 1640 supplemented with 10% foetal calf serum, 2 mM glutamine and Penicillin-Streptomycin (at 50 μg streptomycin/ml, Gibco BRL). THP-1 cells were washed in HBSS (lacking $Ca^{2+}$ and $Mg^{2+}$) +1 mg/ml BSA and resuspended in the same buffer at a density of $3\times10^6$ cells/ml. The cells were then loaded with 1 mM-FURA-2/AM for 30 min at 37° C., washed twice in HBSS, and resuspended at $1\times10^6$ cells/ml. THP-1 cell suspension (0.9 ml) was added to a 5 ml disposable cuvette containing a magnetic stirrer bar and 2.1 ml of prewarmed (37° C.) HBSS containing 1 mg/ml BSA, 1 mM $MgCl_2$ and 2 mM $CaCl_2$. The cuvette was placed in a fluorescence spectrophotometer (Perkin Elmer, Norwalk, Conn.) and pre-incubated for 4 min at 37° C. with stirring. Fluorescence was recorded over 70 sec and cells were stimulated by addition of hMCP-1 to the cuvette after 10 sec. $[Ca^{2+}]i$ was measured by excitation at 340 nm and 380 nm alternately and subsequent measurement of the intensity of the fluorescence emission at 510 nm. The ratio of the intensities of the emitted fluorescent light following excitation at 340 nm and 380 nm, (R), was calculated and displayed to give and estimate of cytoplasmic $[Ca^{2+}]$ according to the equation:

$$[Ca^{2+}]i = K_d \frac{(R - Rmin)}{(Rmax - R)}(Sf2/Sb2)$$

where the $K_d$ for FURA-2 $Ca^{2+}$ complex at 37° C. was taken to be 224 nm. $R_{max}$ is the maximal fluorescence ratio determined after addition of 10 mM Ionomycin, $R_{min}$ is the minimal ratio determined by the subsequent addition of a $Ca^{2+}$ free solution containing 5 mM EGTA, and Sf2/Sb2 is the ratio of fluorescence values at 380 nm excitation determined at $R_{min}$ and $R_{max}$, respectively.

Stimulation of THP-1 cells with hMCP-1 induced a rapid, transient rise in $[Ca^{2+}]i$ in a specific and dose dependent manner. Dose response curves indicated an approximate $EC_{50}$ of 2 nm. Test compounds dissolved in DMSO (10 μl) were assayed for inhibition of calcium release by adding them to the cell suspension 10 sec prior to ligand addition and measuring the reduction in the transient rise in $[Ca^{2+}]i$. Test compounds were also checked for lack of agonism by addition in place of hMCP-1.

c) hMCP-1 Mediated Chemotaxis and RANTES Assay.

In vitro chemotaxis assays were performed using either the human monocytic cell line THP-1 or peripheral blood mixed monocytes obtained from fresh human blood purified by erythrocyte sedimentation followed by density gradient centrifugation over 9.6% (w/v) sodium metrizoate and 5.6% (w/v) polysaccharide, density 1.077 g/ml (Lymphoprep™ Nycomed). Cell migration through polycarbonate membranes was measured by enumerating those passing through either directly by Coulter counting or indirectly by use of a colourimetric viability assay measuring the cleavage of a tetrazolium salt by the mitochondrial respiratory chain (Scudiero D. A. et al. 1988, Cancer Res., 48, 4827–4833).

Chemoattractants were introduced into a 96-well microtiter plate which forms the lower well of a chemotaxis chamber fitted with a PVP-free 5 μm poresize polycarbonate adhesive framed filter membrane (NeuroProbe MB series, Cabin John, Md. 20818, USA) according to the manufacturer's instructions. The chemoattractant was diluted as appropriate in synthetic cell culture medium, RPMI 1640 (Gibco) or supplemented with 2 mM glutamine and 0.5% BSA, or alternatively with HBSS with Ca2+ and Mg2+ without Phenol Red (Gibco) plus 0.1% BSA. Each dilution was degassed under vacuum for 30 min and was placed (400 μl) in the lower wells of the chamber and THP-1 cells ($5\times10^5$ in 100 μl RPMI 1640+0.5% BSA) were incubated in each well of the upper chamber. For the inhibition of chemotaxis the chemoattractant was kept at a constant submaximal concentration determined previously for each chemokine (1 nM for MCP-1 and 2 nM for RANTES) and added to the lower well together with the test compounds dissolved in DMSO (final DMSO concentration <0.05% v/v) at varying concentrations. The chamber was incubated for 2 h at 37° C. under 5% $CO_2$. The medium was removed from the upper wells which were then washed out with 200 μl physiological saline before opening the chamber, wiping dry the membrane surface and centrifuging the 96-well plate at 600 g for 5 min to harvest the cells. Supernatant (150 μl) was aspirated and 10 μl of cell proliferation reagent, WST-1, {4-[3-(4-iodophenyl)-2(4-nitrophenyl)-2H-5-tetrazolio]-1,3-phenyl disulfonate} plus a electron coupling reagent (Boehringer Mannheim, Cat.no. 1644 807) was added back to the wells. The plate was incubated at 37° C. for 3 h and the absorbance of the soluble formazan product was read on a microtitre plate reader at 450 nm. The data was input into a spreadsheet, corrected for any random migration in the absence of chemoattractant and the average absorbance values, standard error of the mean, and significance tests were calculated. hMCP-1 induced concentration dependent cell migration with a characteristic biphasic response, maximal 0.5–1.0 nm.

In an alternative form of the above assay, fluorescently tagged cells can be used in order to assist in end point detection. In this case, the THP-1 cells used are fluorescently tagged by incubation in the presence of 5 mM Calcein AM (Glycine, N,N'-[[3',6'-bis(acetyloxy)-3-oxospiro [isobenzofuran-1 (3H),9'-[9H]xanthene]-2',7'-diyl]bis (methylene)]bis[N-[2-[(acetyloxy)methoxy]-2-oxoethyl]]-bis[(acetyloxy)methyl] ester: Molecular Probes) for 45 minutes in the dark. Cells are harvested by centrifugation and resuspended in HBSS (without Phenol Red) with Ca2+, Mg2+ and 0.1% BSA. 50 ml ($2\times105$ cells) of the cell suspension are placed on the filter above each well and, as above, the unit is incubated at 37° C. for 2 hours under 5% CO2. At the end of the incubation, cells are washed off the upper face of the filter with phosphate buffered saline, the filter removed from the plate and the number of cells attracted to either the underside of the filter or the lower well estimated by reading fluorescence at 485 nm excitation, 538 nm emission wavelengths (fmax, Molecular Devices). The data was input into a spreadsheet, corrected for any random migration in the absence of chemoattractant and the average fluorescence values, standard error of the mean, percentage inhibition and IC50 of compounds under test and significance tests can be calculated.

For example, using this method, compound No. 20 in Table I showed an $IC_{50}$ of 1.66 μM in the hMCP-1 chemotaxis assay and compound No. 8 in Table 1 showed an $IC_{50}$ of 2.66 μM in the RANTES assay.

No physiologically unacceptable toxicity was observed at the effective dose for compounds tested of the present invention.

EXAMPLE 17

Pharmaceutical Compositions

This Example illustrates, but is not intended to limit, representative pharmaceutical dosage forms of the invention as defined herein (the active ingredient being termed "Compound X"), for therapeutic or prophylactic use in humans:

EXAMPLE A (a)

| Tablet I | mg/tablet |
|---|---|
| Compound X. | 100 |
| Lactose Ph.Eur | 182.75 |
| Croscarmellose sodium | 12.0 |
| Maize starch paste (5% w/v paste) | 2.25 |
| Magnesium stearate | 3.0 |

(b)

| Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

(c)

| Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

(d)

| Capsule | mg/capsule |
|---|---|
| Compound X | 10 |
| Lactose Ph.Eur | 488.5 |
| Magnesium | 1.5 |

(e)

| Injection I | (50 mg/ml) |
|---|---|
| Compound X | 5.0% w/v |
| 1 M Sodium hydroxide solution | 15.0% v/v |
| 0.1 M Hydrochloric acid | to adjust pH to 7.6 |
| Polyethylene glycol 400 | 4.5% w/v |
| Water for injection | to 100% |

(f)

| Injection II | (10 mg/ml) |
|---|---|
| Compound X | 1.0% w/v |
| Sodium phosphate BP | 3.6% w/v |
| 0.1 M Sodium hydroxide solution | 15.0% w/v |
| Water for injection | to 100% |

(g)

| Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

(h)

| Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

(i)

| Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

(j)

| Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

(k)

| Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

(l)

| Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note:
Compound X in the above formulations may comprise a compound as illustrated in Examples 1 to 15 herein, for example the compounds of Examples 12 to 15.

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A compound of formula (I):

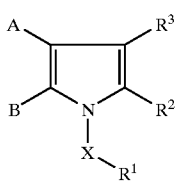

or a pharmaceutically acceptable salt, ester or amide thereof, which is an inhibitor of monocyte chemoattractant protein-1 and wherein A and B together form an optionally substituted 5 membered aromatic ring which includes at least one heteroatom;

X is CH$_2$ or SO$_2$;

R$^1$ is an optionally substituted aryl or heteroaryl ring;

R$^2$ is carboxy, cyano, —C(O)CH$_2$OH, —CONHR$^4$, —SO$_2$NHR$^5$, tetrazol-5-yl, SO$_3$H, or a group of formula (VI):

(VI)

where R$^4$ is selected from the group consisting of hydrogen, alkyl, aryl, cyano, hydroxy, —SO$_2$R$^9$ where R$^9$ is alkyl, aryl, heteroaryl, or haloalkyl, and a group-(CHR$^{10}$)$_r$—COOH where r is an integer of 1–3 and each R$^{10}$ group is independently hydrogen and alkyl; R$^5$ is alkyl, optionally substituted aryl or optionally substituted heteroaryl or a group COR$^6$ where R$^6$ is hydrogen, alkyl, aryl, heteroaryl or haloalkyl; R$^7$ and R$^8$ are independently hydrogen and alkyl; and R$^3$ is hydrogen or a functional group selected from the group consisting of halo, cyano, nitro, oxo, C(O)$_n$R$^{11}$, OR$^{11}$, S(O)$_m$R$^{11}$, NR$^{12}$R$^{12'}$, C(O)NR$^{12}$R$^{12'}$, OC(O)NR$^{12}$R$^{12'}$, —CH=NOR$^{11}$, —NR$^{12}$C(O)$_n$R$^{11}$, —NR$^{11}$CONR$^{12}$R$^{12'}$, —N=CR$^{12}$R$^{12'}$, S(O)$_m$NR$^{12}$R$^{12'}$ and —NR$^{12}$S(O)$_m$R$^{11}$ where R$^{11}$, R$^{12}$ and R$^{12'}$ are independently hydrogen or optionally substituted hydrocarbyl, or R$^{12}$ and R$^{12'}$ together form an optionally substituted ring which optionally contains further heteroatoms, n is an integer of 1 or 2, m is 0 or an integer of 1–3, and wherein optional substituents for hydrocarbyl groups R$^{11}$, R$^{12}$ and R$^{12'}$ are selected from the group consisting of halo, perhaloalkyl, mercapto, hydroxy, alkoxy, oxo, heteroaryloxy, alkenyloxy, alkynyloxy, alkoxyalkoxy, cyano, nitro, amino, mono- or di-alkyl amino, alkylamido, and oximino, and aryloxy where the aryl group may be substituted by halo, nitro, or hydroxy;

or R$^3$ is an optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy or optionally substituted cycloalkyl; subject to the following provisos:

a) that where A—B forms a group of sub-formula (i) or (iv):

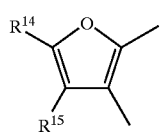

(i)

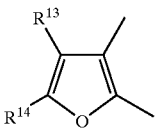

(iv)

where R$^{13}$, R$^{14}$ and R$^{15}$ are independently hydrogen and a substituent group selected from functional groups as defined in respect to R$^3$, R$^1$ is other than phenyl, amino phenyl or nitrophenyl; and b) that where A—B forms a group of sub-formula (iii):

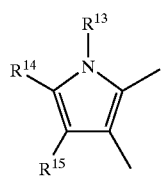

(iii)

where R$^{13}$ is hydrogen, R$^{14}$ is not CHO;

c) that where A—B a group of sub-formula (v):

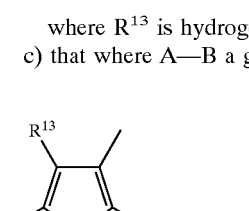

(v)

where R$^{13}$ and R$^{14}$ are as defined above in a), and X is SO$_2$, R$^1$ is other than unsubstituted phenyl.

2. A compound according to claim 1 wherein A and B together with the carbon atoms to which they are attached form a 5 membered heteroaryl ring of any one of the sub-formulae:

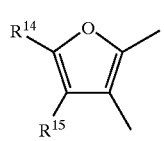

(i)

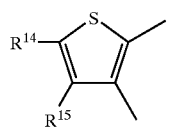

(ii)

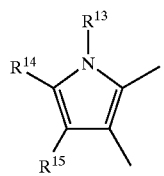

(iii)

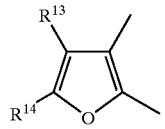

(iv)

-continued

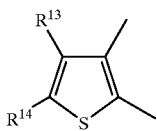
(v)

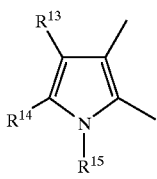
(vi)

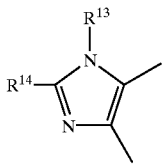
(vii)

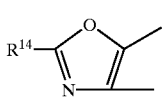
(viii)

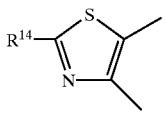
(ix)

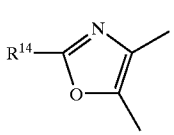
(x)

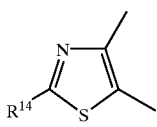
(xi)

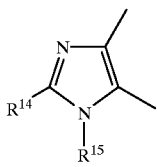
(xii)

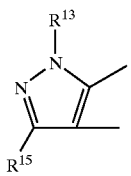
(xiii)

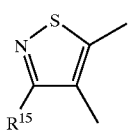
(xiv)

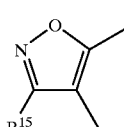
(xv)

-continued

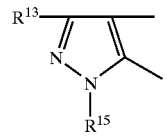
(xvi)

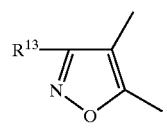
(xvii)

or

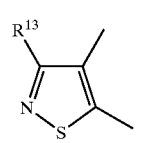
(xviii)

where $R^{13}$, $R^{14}$ and $R^{15}$ are independently hydrogen, a functional group as defined in claim 1 with respect to $R^3$, or an optionally substituted hydrocarbyl group selected from the group consisting of alkyl, cycloalkyl, alkenyl, cycloalkenyl, alkynyl, and cycloalkynyl.

3. A compound according to claim 1 where $R^1$ is a halo-substituted phenyl or pyridyl group.

4. A compound according to claim 1 wherein in the compound of formula (I), $R^2$ is carboxy; or a pharmaceutically acceptable salt or ester thereof.

5. A compound according to claim 1 wherein $R^3$ is hydrogen, $C_{1-4}$alkyl or trifluoromethyl.

6. A compound of formula (IA) or (IB) as claimed in claim 1:

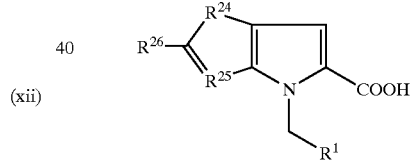
(IA)

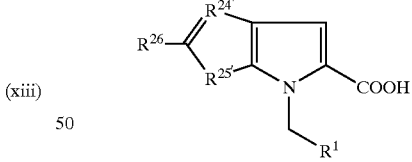
(IB)

or a pharmaceutically acceptable salt, ester or amide thereof, where $R^1$ is an optionally substituted aryl or heteroaryl ring, $R^{26}$ is hydrogen or $C_{1-4}$ alkyl, and in formula (IA)
 (i) $R^{24}$ is sulphur and $R^{25}$ is CH; or
 (ii) $R^{24}$ is sulphur and $R^{25}$ is nitrogen; or
 (iii) $R^{24}$ is oxygen and $R^{25}$ is CH; or
 (iv) $R^{24}$ is $NCH_3$ and $R^{25}$ is CH;
and in formula (IB)
 (i) $R^{24'}$ is CH and $R^{25'}$ is sulphur; or
 (ii) $R^{24'}$ is CH and $R^{25'}$ is oxygen; or
 (iii) $R^{24'}$ is nitrogen and $R^{25'}$ is sulphur.

7. A pharmaceutical composition comprising a compound of formula (I):

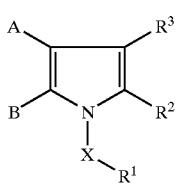

or a pharmaceutically acceptable salt, ester or amide thereof, which is an inhibitor of monocyte chemoattractant protein-1 and wherein A and B together form a ring of structure (i):

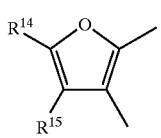

where $R^{14}$ and $R^{15}$ are independently hydrogen or a functional group selected from the group consisting from halo, cyano, nitro, oxo, $C(O)_n R^{11}$, $OR^{11}$, $S(O)_m R^{11}$, $NR^{12}R^{12'}$, $C(O)NR^{12}R^{12'}$, $OC(O)NR^{12}R^{12'}$, —CH=NOR$^{11}$, —NR$^{12}$C(O)$_n$R$^{11}$, —NR$^{11}$CONR$^{12}$R$^{12'}$, —N=CR$^{12}$R$^{12'}$, $S(O)_m NR^{12}R^{12'}$ and —NR$^{12}$S(O)$_m$R$^{11}$ where $R^{11}$, $R^{12}$ and $R^{12'}$ are independently hydrogen or optionally substituted hydrocarbyl, or $R^{12}$ and $R^{12'}$ together form an optionally substituted ring which optionally contains further heteroatoms, n is an integer of 1 or 2, m is 0 or an integer of 1–3, and wherein optional substituents for hydrocarbyl groups $R^{11}$, $R^{12}$ and $R^{12'}$ are selected from the group consisting from halo, perhaloalkyl, mercapto, hydroxy, alkoxy, oxo, heteroaryloxy, alkenyloxy, alkynyloxy, alkoxyalkoxy, cyano, nitro, amino, mono- or di-alkyl amino, alkylamido, oximino, an optionally substituted alkyl, cycloalkyl, alkenyl, cycloalkenyl, alkynyl, cycloalkynyl and aryloxy group, where the aryl group may be substituted by halo, nitro, or hydroxy;

X is CH$_2$ or SO$_2$;

$R^1$ is a halo-substituted phenyl or pyridyl group;

$R^2$ is carboxy, cyano, —C(O)CH$_2$OH, —CONHR$^4$, —SO$_2$NHR$^5$, tetrazol-5-yl, SO$_3$H, or a group of formula (VI):

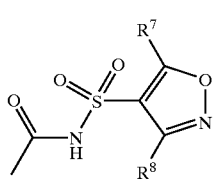

where $R^4$ is selected from the group consisting from hydrogen, alkyl, aryl, cyano, hydroxy, and —SO$_2$R$^9$ where $R^9$ is alkyl, aryl, heteroaryl, or haloalkyl or $R^4$ is a group -(CHR$^{10}$)$_r$—COOH where r is an integer of 1–3 and each $R^{10}$ group is independently hydrogen and alkyl; $R^5$ is alkyl, optionally substituted aryl or optionally substituted heteroaryl or a group COR$^6$ where $R^6$ is hydrogen, alkyl, aryl, heteroaryl or haloalkyl; $R^7$ and $R^8$ are independently hydrogen and alkyl; and $R^3$ is hydrogen, or a functional group selected from the group consisting of halo, cyano, nitro, oxo, $C(O)_n R^{11}$, $OR^{11}$, $S(O)_m R^{11}$, $NR^{12}R^{12'}$, $C(O)NR^{12}R^{12'}$, $OC(O)NR^{12}R^{12'}$, —CH=NOR$^{11}$, —NR$^{12}$C(O)$_n$R$^{11}$, —NR$^{11}$CONR$^{12}$R$^{12'}$, —N=CR$^{12}$R$^{12'}$, $S(O)_m NR^{12}R^{12'}$ and —NR$^{12}$S(O)$_m$R$^{11}$ where $R^{11}$, $R^{12}$ and $R^{12'}$ are independently hydrogen or optionally substituted hydrocarbyl, or $R^{12}$ and $R^{12'}$ together form an optionally substituted ring which optionally contains further heteroatoms, n is an integer of 1 or 2, m is 0 or an integer of 1–3, and wherein optional substituents for hydrocarbyl groups $R^{11}$, $R^{12}$ and $R^{12'}$ are selected from the group consisting of halo, perhaloalkyl, mercapto, hydroxy, alkoxy, oxo, heteroaryloxy, alkenyloxy, alkynyloxy, alkoxyalkoxy, cyano, nitro, amino, mono- or di-alkyl amino, alkylamido, oximino, and aryloxy where the aryl group may be substituted by halo, nitro, or hydroxy;

or $R^3$ is an optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy or optionally substituted cycloalkyl;

in combination with a pharmaceutically acceptable carrier.

8. A pharmaceutical composition comprising a compound of formula (I):

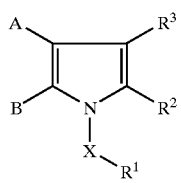

or a pharmaceutically acceptable salt, ester or amide thereof, which is an inhibitor of monocyte chemoattractant protein-1 and wherein A and B together with the carbon atoms to which they are attached form a 5 membered heteroaryl ring of any one of the sub-formulae (ii) to (xvii):

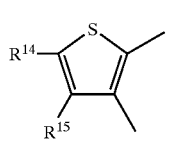

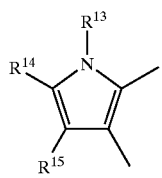

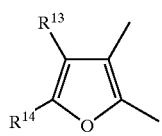

-continued (v) 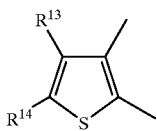

(vi) 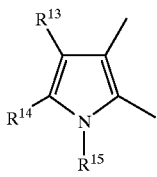

(vii) 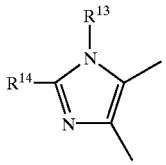

(viii) 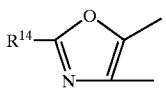

(ix) 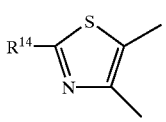

(x) 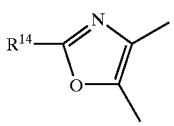

(xi) 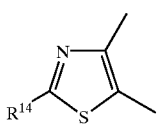

(xii) 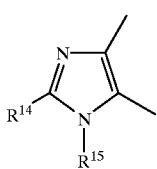

(xiii) 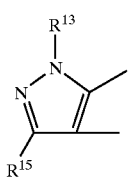

(xiv) 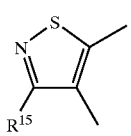

(xv) 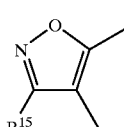

(xvi) 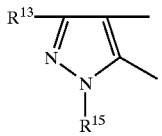

(xvii) 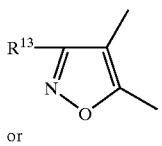

or (xviii) 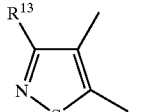

where $R^{13}$, $R^{14}$ and $R^{15}$ are independently hydrogen or a functional group selected from the group consisting of halo, cyano, nitro, oxo, $C(O)_nR^{11}$, $OR^{11}$, $S(O)_mR^{11}$, $NR^{12}R^{12'}$, $C(O)NR^{12}R^{12'}$, $OC(O)NR^{12}R^{12'}$, —CH=NOR$^{11}$, —NR$^{12}$C(O)$_n$R$^{11}$, —NR$^{11}$CONR$^{12}$R$^{12'}$, —N=CR$^{12}$R$^{12'}$, $S(O)_m$NR$^{12}$R$^{12'}$ and —NR$^{12}$S(O)$_m$R$^{11}$ where $R^{11}$, $R^{12}$ and $R^{12'}$ are independently hydrogen or optionally substituted hydrocarbyl, or $R^{12}$ and $R^{12'}$ together form an optionally substituted ring which optionally contains further heteroatoms, n is an integer of 1 or 2, m is 0 or an integer of 1–3, and wherein optional substituents for hydrocarbyl groups $R^{11}$, $R^{12}$ and $R^{12'}$ are selected from the group consisting of halo, perhaloalkyl, mercapto, hydroxy, alkoxy, oxo, heteroaryloxy, alkenyloxy, alkynyloxy, alkoxyalkoxy, cyano, nitro, amino, mono- or di-alkyl amino, alkylamido, oximino an optionally substituted alkyl, cycloalkyl, alkenyl, cycloalkenyl, alkynyl, cycloalkynyl and aryloxy group where the aryl group may be substituted by halo, nitro, or hydroxy;

X is $CH_2$ or $SO_2$;

$R^1$ is an optionally substituted aryl or heteroaryl ring;

$R^2$ is carboxy, cyano, —C(O)CH$_2$OH, —CONHR$^4$, —SO$_2$NHR$^5$, tetrazol-5-yl, SO$_3$H, or a group of formula (VI):

(VI) 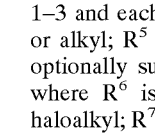

where $R^4$ is selected from the group consisting of hydrogen, alkyl, aryl, cyano, hydroxy, —SO$_2$R$^9$ where $R^9$ is alkyl, aryl, heteroaryl, or haloalkyl, and a group-(CHR$^{10}$)$_r$—COOH where r is an integer of 1–3 and each $R^{10}$ group is independently hydrogen or alkyl; $R^5$ is alkyl, optionally substituted aryl, or optionally substituted heteroaryl or a group COR$^6$ where $R^6$ is hydrogen, alkyl, aryl, heteroaryl or haloalkyl; $R^7$ and $R^8$ are independently selected from hydrogen and alkyl; and R³ is hydrogen, or a functional group selected from the group consisting of halo, cyano, nitro, oxo, C(O)$_n$R¹¹, OR¹¹, S(O)$_m$R¹¹, NR¹²R¹²', C(O)NR¹²R¹²', OC(O)NR¹²R¹²', —CH=NOR¹¹, —NR¹²C(O)$_n$R¹¹, —NR¹¹CONR¹²R¹²', —N=CR¹²R¹²', S(O)$_m$NR¹²R¹²' and —NR¹²S(O)$_m$R¹¹ where R¹¹, R¹² and R¹²' are independently hydrogen or optionally substituted hydrocarbyl, or R¹² and R¹²' together form an optionally substituted ring which optionally contains further heteroatoms, n is an integer of 1 or 2, m is 0 or an integer of 1–3, and wherein optional substituents for hydrocarbyl groups R¹¹, R¹² and R¹²' are selected from the group consisting of halo, perhaloalkyl, mercapto, hydroxy, alkoxy, oxo, heteroaryloxy, alkenyloxy, alkynyloxy, alkoxyalkoxy, cyano, nitro, amino, mono- or di-alkyl amino, alkylamido, oximino, and aryloxy group where the aryl group may be substituted by halo, nitro, or hydroxy;

or R³ is an optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy or optionally substituted cycloalkyl;

in combination with a pharmaceutically acceptable carrier.

9. A pharmaceutical composition comprising a compound according to claim 1 in combination with a pharmaceutically acceptable carrier.

10. A composition according to claim 8 where R¹ is a halo-substituted phenyl or pyridyl group.

11. A composition according to any one of claims 7 or 8 wherein R² is carboxy; or a pharmaceutically acceptable salt or ester thereof.

12. A composition according to any one of claims 7 or 8 wherein R³ is hydrogen, C$_{1-4}$alkyl or trifluoromethyl.

13. A composition according to any one of claims 7, 8 or 9, wherein R⁵ is optionally substituted phenyl or optionally substituted 5 or 6 membered heteroaryl group.

14. A composition according to any one of claims 7, 8 or 9, wherein R⁷ and R⁸ are independently selected from hydrogen or C$_{1-4}$ alkyl.

15. A method of preparing a compound of formula (I) as defined in claim 1, which method comprises reacting a compound of formula (VII):

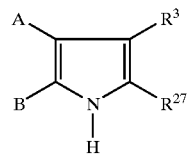
(VII)

where A, B and R³ are as defined in relation to formula (I) and R²⁷ is either hydrogen or a group R² as defined in claim 1 in relation to formula (I); with compound of formula (VIII):

R¹—X—Z (VIII)

where R¹ and X are as defined in relation to formula (I) and Z is a leaving group.

16. A method according to claim 15, further comprising at least one of the following steps a) and b):
a) converting the group R²⁷ into a group selected from the group consisting of carboxy, cyano, —C(O)CH₂OH, —CONHR⁴, —SO₂NHR⁵, tetrazol-5-yl, SO₃H, and a group of formula (VI):

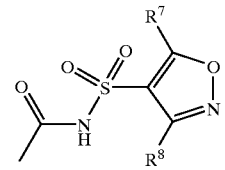
(VI)

where R⁴ is selected from the group consisting of hydrogen, alkyl, aryl, cyano, hydroxy, —SO₂R⁹ where R⁹ is alkyl, aryl, heteroaryl, haloalkyl, and a group-(CHR¹⁰)$_r$—COOH where r is an integer of 1–3 and each R¹⁰ group is independently hydrogen and alkyl; R⁵ is alkyl, optionally substituted aryl or optionally substituted heteroaryl or a group COR⁶ where R⁶ is hydrogen, alkyl, aryl, heteroaryl or haloalkyl; R⁷ and R⁸ are independently hydrogen and alkyl;
b) adding substituents to the A—B ring or converting substituents into different substituent groups in the A—B ring.

17. A method according to claim 16, wherein said steps a) and b) are conducted subsequent to reacting the compound of formula (VII) with the compound of formula (VIII).

* * * * *